United States Patent [19]
Bierer et al.

[11] Patent Number: 5,648,354
[45] Date of Patent: Jul. 15, 1997

[54] 1,2-DITHIINS HAVING ANTIFUNGAL ACTIVITY

[75] Inventors: Donald E. Bierer; Jeffrey M. Dener, both of Daly City; Joane Litvak, Oakland; Larisa G. Dubenko, San Francisco, all of Calif.

[73] Assignee: Shaman Pharmaceuticals, Inc., South San Francisco, Calif.

[21] Appl. No.: 395,777

[22] Filed: Feb. 28, 1995

Related U.S. Application Data

[63] Continuation-in-part of Ser. No. 212,096, Mar. 11, 1994, Pat. No. 5,583,235.
[51] Int. Cl.$^6$ ........................ C07D 339/08; A61K 31/385
[52] U.S. Cl. .................... 514/252; 514/336; 514/382; 514/397; 514/436; 544/239; 546/280.1; 548/252; 548/341.1; 549/22
[58] Field of Search .................. 549/20, 22; 514/436, 514/252, 336, 382, 397; 546/280.1; 544/239; 548/252, 341.1

[56] References Cited

U.S. PATENT DOCUMENTS

| | | | |
|---|---|---|---|
| 4,659,733 | 4/1987 | DuPriest et al. | 514/436 |
| 5,202,348 | 4/1993 | Towers et al. | 514/436 |
| 5,453,500 | 9/1995 | Koreeda et al. | 536/123 |

FOREIGN PATENT DOCUMENTS

| | | |
|---|---|---|
| 2118437 | 10/1972 | Germany. |
| WO95/05817 | 3/1995 | WIPO. |

OTHER PUBLICATIONS

Dzhemilev et al., 1986, "A new catalytic reaction of elemental sulfur with acetylenes by the action of cobalt complexes", *Izv. Akad. Nauk SSSR, Ser. Khim.* 5:1211–1212.

Dzhemilev et al., 1987, "An original method for the preparation of sulfides and disulfides involving cobalt complexes", *Izv. Akad. Nauk SSSR, Ser. Khim.* 8:1918.

Mao et al., 1994, "In vitro Evaluation of a Series of Novel Substituted 1,2-Dithiins", XII Congress of the International Society for Human and Animal Mycology, Adelaide, South Australia, Mar. 13–18.

Koreeda and Yang, "Chemistry of 1,2-Dithiins. Synthesis of the Potent Antibiotic Thiarubrine A", *J Am Chem Soc* 116:10793–10794, 1994.

Koreeda and Yang, 1994, "The Chemistry of 1,2-Dithiins: Synthesis of 1,2-Dithiin and 3,6-Disubstituted 1,2-Dithiins", Synlett 201–203.

Block et al., 1994, "Total Synthesis of Thiarubrine B [3-(3-Buten-1-ynyl)-6-(1,3-pentadiynyl)-1,2-dithiin], the Antibiotic Principle of Giant Ragweed (*Ambrosia trifida*)", *J Am Chem Soc* 116:9403–9404.

Freeman et al., 1993, "Naturally Occurring 1,2-Dithiins" in Reviews on Heteroatom Chemistry; Oae, S., Ed., Tokyo pp. 1–19.

Hudson et al., 1993, "Light-Mediated Activities of Thiarubrines Against Human Immunodeficiency Virus", Photochemistry and Photobiology 57:675–680.

Yang and Koreeda, 1993, American Chemical Society, Division of Organic Chemistry, 206th National Meeting, Aug. 22–27 1993, Abstract 349.

Ellis et al., 1993, "A Diathiacyclohexadiene Polyyne Alcohol from *Ambrosia chamissonis*", Phytochemistry 33:224–228.

Gomez-Barrios et al., 1992, "Studies on the Biosynthesis of Thiarubrine A in Hairy Root Cultures of *Ambrosia artemisiifolia* Using $^{13}$C–Labelled Acetates", Phytochemistry 31:2703–2707.

Cimiraglia et al., 1991, "An ab initio Study of the Structure and Electronic spectrum of 1,2-Dithiete and 1,2-Dithiin", J Mol Struct (Therochem). 230:287–293.

Greene and Wuts, "Protective Groups in Organic Synthesis", John Wiley & Sons, Inc., New York, 1991, p. 296.

Aihara et al., 1990, "Chemical Evolution, Biosynthesis, and Aromaticity", J Bull Chem Soc Jpn, 63:2899–2903.

Balza et al., 1990, "Dithiacyclohexadiene Chlorohydrins and Related Sulphur Containing Polyynes from *Ambrosia chamissonis*", Phytochemistry 29:2901–2904.

Balza et al., 1989, "Dithiacyclohexadienes and Thiophense from *Ambrosia chamissonis*", Phytochemistry 28(12):3523–3524.

Constabel et al., 1989, "Incorporation of $^{35}$S into Dithiacyclohexadiene and Thiophene Polyines in Hairy Root Cultures of *Chaenactis douglasii*", Phytochemistry 38:93–95.

Freeman et al., 1989, "The Chemistry of 1,2-Dithiins", Sulfur Reports 9(3):207–256.

Constabel et al., 1989, "The Complex Nature of the Mechanism of Toxicity of Antibiotic Dithiacyclohexadiene Polyines (Thiarubrines) from the Asteraceae", Planta Med 55:35–37.

(List continued on next page.)

*Primary Examiner*—Zinna Northington Davis
*Attorney, Agent, or Firm*—Pennie & Edmonds

[57] ABSTRACT

Novel 1,2-dithiin compounds useful as antifungal or anti-infective agents, as well as methods for their use as such, are described. The 1,2-dithiin compounds are particularly effective in treating infections, especially those caused by *Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, Histoplasma capsulatum,* Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdovirus, Togavirus, Hepadnavirus, *Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia,* Acinetobacter, *Enterobacter cloacae, Serratia marscens, Listeria, Monocytogenes, Enterococcus faecalis, Streptococcus pyogenes; Streptococcus pneumonia, Viridans streptococci, Haemophilus influenzae, Proteus mirabills, Proteus vulgaris* and *Bacterioides fragilis.*

9 Claims, 5 Drawing Sheets

OTHER PUBLICATIONS

Fabian and Birner, 1988, "A Theoretical Study of the Disulfide/Dithione Valence Isomerism", Coll Czech Chem Comm 53:2096–2115.

Hudson et al., 1986, "Comparison of the Antiviral Effects of Naturally Occurring Thiophenes and Polyacetylenes", N Planta Medica 52:453–457.

Hudson et al., 1986, "Antiviral Properties of Thiarubrine–A, a Naturally Occurring Polyine", Planta Med 52:51–54.

Cosio et al., 1986, "Production of Antibiotic Thiarubrines by a Crown Gall Tumor Line of *Chaenactis douglasii*", J Plant Physiol 124:155–164.

Towers et al., 1985, "Antibiotic Properties of Thiarubrine A, a Naturally Occurring Dithiacyclohexadiene Polyine", Planta Medica 51:225–229.

Rodriguez et al., 1985, "Thiarubrine A, a Bioactive Constituent of *Aspilia* (Asteraceae) Consumed by Wild Chimpanzees", N Experiementa 41:419–420.

Kokwaro, 1976, Medicinal Plants of East Africa, East African Literature Bureau, pp. 58–76.

Ried and Ochs, 1972, "Electrophilic Addition of Disulfur Dichloride (S2Cl2 to Alkynes", Chemical Abstracts 77:433, Abstract 4826m.

Schroth et al., 1967, "1,2–Dithiins, a New Type of Heterocycle", Angew Chem, Int Ed Eng 6:698–699.

Schroth et al., 1966, "Stereoisomeric 1,4–dimercaptobutadiene", Chemical Abstracts vol. 64, Abstract 3339a.

Bohlmann and Kleine, 1965, "Uber rote Naturliche Schwefelacetylenverbindungen", M Chem Ber 98:3081–3086.

Mortensen et al., 1964, "Studies Related to Naturally Occurring Acetylene Compounds", Acta Chem Scand 18:2392–2394.

Ellis et al, Phytochemistry, vol. 33, No. 1, 1993, pp. 224–226.

Koreeda et al, Synlett, 1994, pp. 201–203.

Fabian et al, Collect. Czech. Chem. Commun, vol. 53, No. 9, 1988, pp. 2096–2115.

Freeman et al, Sulfur Reports, vol. 9, No. 3, 1989, pp. 207–256.

1,2-DITHIINS HAVING ANTIFUNGAL ACTIVITY

The present application is a continuation-in-part of application Ser. No. 08/212,096 filed Mar. 11, 1994, now U.S. Pat. No. 5,583,235 which is incorporated herein by reference in its entirety.

FIELD OF THE INVENTION

This invention pertains to a novel group of 1,2-dithiin compounds and their use as antifungal or anti-infective agents.

BACKGROUND OF THE INVENTION 1,2-Dithiins are six-membered antiaromatic heterocycles having a disulfide linkage in place of the two contiguous CH groups of benzene. [Cimiraglia, R.; Fabian, J.; Hess, B. A., Jr. *J. Mol. Struct.* (Therochem) 1991, 230, 287–293; Aihara, J. *Bull. Chem. Soc. Jpn.* 1990, 63, 2899–2903]. The 1,2-dithiin class of heterocycles have been of interest due to their interesting physical and biological properties. Ten natural products containing this unique heterocycle have been isolated since the 1960's, primarily from plants of the family Asteraceae (Mortensen, J. T., Sorensen, J. S., Sorensen, N. A.; *Acta Chem. Scand.* 1964, 18, 2392–2394; Bohlmann, F. Klein, K., *M. Chem. Ber.* 1965, 98, 3081–3086; Kokwaro, J. O., Medicinal Plants of East Africa; East African Literature Bureau, Nairobi, Kenya: 1976, pgs. 58–76; Rodriguez, E.; Aregullin, M.; Nishida, T.; Uehara, S.; Wrangham, R. W.; Abramowski, Z.; Finlayson, A. J.; Towers, G. H. N. *Experimentia*, 1985, 41, 419–420.; Gomez-Barrios, M. L.; Parodi, F. J.; Vargas, D.; Quijano, L; Hjortso, M. A.; Flores, H. E.; Fisher, N. H. *Phytochemistry*, 1992, 31, 2703–2707; Constabel, C. P.; Towers, G. H. N. *Phytochemistry*, 1989, 28, 93–95). Among these natural products is thiarubrine A, which was isolated from leaves of *Aspilia mossamblcesis* and *Aspilia plurisetta*, (Rodriquez, E.; Aregullin, M.; Nishida, T.; Uehara, S.; Wrangham, R. W.; Abramowski, Z.; Finlayson, A. J.; Towers, G. H. N., *Experimentia*, 1985, 41, 419–420), from the roots of *Chaenactis douglasii* and *Ambrosia chamissonis* (Ellis, S.; Balza, F.; Towers, G. H. N. *Phytochemistry*, 1993, 33, 224–228 Balza, F.; Towers, G. H. N. *Phytochemistry*, 1990, 29, 2901–2904) and from the roots of *Ambrosia artemisiifolia* (Gomez-Barrios, M. L.; Parodi, F. J.; Vargas, D.; Quijaro, L.; Hjortso, M. A.; Flores, H. E.; Fischer, N. H., *Phytochemistry*, 1992, 31, 2703–2707). Thiarubrine A has been shown to possess both antifungal and antiviral activity but is also cytotoxic (Constabel, C. P.; Towers, G. H. N., *Planta Med.*, 1989, 55, 35–37; Towers, G. H. N.; Abramowski, Z.; Finlayson, A. J.; Zucconi, A., *Planta Med.*, 1985, 51, 225–229; Hudson, J. B.; Graham, E. A.; Fong, R.; Finlayson, A. G.; Towers, G. H. N., *Planta Med.*, 1986, 52, 51–54). Other thiarubrines which possess antifungal and antibacterial activity have been described (Towers, G. H. N.; Bruening, R. C. B.; Balza, F.; Abramowski, Z. A.; Lopez-Bazzochi, I. U.S. Pat. No. 5,202,348, Apr. 13, 1993; Balza, F.; Towers, G. H. N., *Phytochemistry*, 1990, 29, 2901–2904). Such compounds are both heat and light sensitive, and easily convertible to their corresponding thiophenes under proper thermal or photochemical conditions. All of the natural products possess acetylenic sidechains in the 3- and 6-positions of the dithiin, which may in part account for their instability. Additionally, compounds related to dithiins have been known to possess antiviral, antibacterial, and antifungal activities (Hudson, J. R.; Graham, E. A.; Chan, G.; Finlayson, A. J.; Towers, G. H. N. *Planta Med.* 1986, 52, 453–457; Cosio, E.G.; Norton, R. N.; Towers, E.; Finlayson, A. J.; Rodriguez, E.; Towers, G. H. N. *J. Plant Physiol.* 1986, 124, 155–164). Naturally occurring 1,2-dithiins have also been isolated from the roots and leaves of *Chaenactis douglasii*, root cultures of *Eriophyllum ianatum, Rudbeckia hirta, Ambrosia chamissonis, Aspilia mossambicensis, Aspilia pluriseta, Aspilia rudis,* and other species of Asteraceae (Freeman, F.; Aregullin, M.; Rodriguez, E. "Naturally Occurring 1,2-Dithiins" in Reviews on Heteroatom Chemistry; Oae, S., Ed., MYU:Tokyo 1993; vol. 9, pp. 1–19; Freeman, F.; Kim, D. S. H. L.; Rodriquez, E. "The Chemistry of 1,2-Dithiins" in Sulfur Reports; Senning, A. Ed., Langhorne, Pa. 1989; vol 9, pp. 207–256). In addition to the observed antifungal, antiviral, antibacterial, and cytotoxic activities which the natural 1,2-dithiins (thiarubrines) possess, some naturally occuring 1,2-dithiins have been shown to possess light mediated antiviral activity against the human immunodeficiency virus (Hudson, J. B.; Balza, F.; Harris, L.; Towers, G. H. N. Photochem. and Photobiol. 1993, 57, 675–680), and nematocidal activity and antitumor properties (Freeman, F.; Aregullin, M.; and Rodriguez, E. "Naturally Occurring 1,2-Dithiins" in Reviews on Heteroatom Chemistry, Oae, S., Ed., MYU:Tokyo, 1993; vol. 9, pp. 1–19.

The total synthesis of two naturally occurring 1,2-dithiins (thiarubrine A and thiarubrine B) have been reported (Block, E.; Guo, C.; Thiruvazhi, M.; Toscano, P. J., *J. Am. Chem. Soc.* 1994, 116, 9403; Koreeda, M.; Yang, W., *J. Am. Chem. Soc.*, 1994, 116, 10793–10794). Abstract 349 of W. Wang and M. Koreeda, American Chemical, Society, Division of Organic Chemistry. 206th National Meeting, Aug. 22–27, 1993 describes the synthesis of 1,2-dithiins from regioselective bisaddition of benzylthiol to 1,4-disubstituted diynes. Abstract of Mao et al., XII Congress of the International Society for Human and Animal Mycology, Adelaide, South Austrailia, Mar. 13–18, 1994, describes synthetic mono and diester dithiin derivatives having fungicidal activity.

The preparation of 1,2-dithiin and its 3,6-disubstituted analogs have been reported (Schroth, W.; Billig, F.; Reinhold, G. *Angew. Chem., Int. Ed. Engl.* 1967, 6, 698–699). The synthesis of certain 1,2-dithiin analogs has further been described (M. Koreeda and W. Yang, Synlett, 1994, 201–203).

Citation or identification of any reference in Section 2 of this application shall not be construed as an admission that such reference is available prior art to the invention.

Due to the natural products' inherent cytotoxicity and extreme instability to light, these substances have obvious disadvantages for use as therapeutic agents. Thus there is a need for antifungal agents which are neither inherently cytotoxic nor extremely unstable to light.

To the knowledge of the inventors, no prior study has described any antifungal or anti infective activity of 1,2-dithiin compounds lacking acetylenic, mono or diester moieties, nor has there been any suggestion in the prior art that such compounds of the present invention would be useful as such.

SUMMARY OF THE INVENTION

The present invention provides novel 1,2-dithiin compounds, as well as pharmaceutically acceptable salts thereof, having antifungal or anti infective activity, pharmaceutical compositions comprising the novel 1,2-dithiins of the present invention, as well as methods for their use. Particularly, the invention provides novel 1,2-dithiins having the formula I:

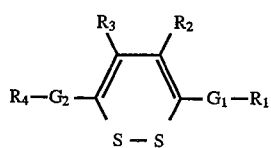

and pharmaceutically acceptable salts thereof, wherein:

$R_2$ and $R_3$ are hydrogen;

$G_1$ and $G_2$ are independently selected from the group consisting of a $C_1$–$C_{10}$ alkyl or branched alkyl group and a $C_3$–$C_{10}$ cycloalkyl group;

$R_1$ and $R_4$ are independently selected from the group consisting of hydrogen, —OH, —$OR_5$, —O(CO)$R_5$, —$SR_6$ or a pyridone radical of the type:

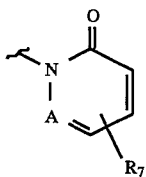

wherein $R_7$ is selected from the group consisting of hydrogen, —OH, —SH, —$NO_2$, —$NH_2$, halogen, trifluoromethyl, —CHO, —COOH, —$COOR_8$, —$OR_8$ and $SR_8$;

A is nitrogen or carbon;

$R_8$ is an alkyl group of 1 to 6 carbon atoms;

$R_5$ and $R_6$ are independently selected from the group consisting of a $C_1$–$C_{20}$ alkyl group, a $C_1$–$C_{20}$ alkenyl group, a $C_3$–$C_{10}$ cycloalkyl group and a radical of the type:

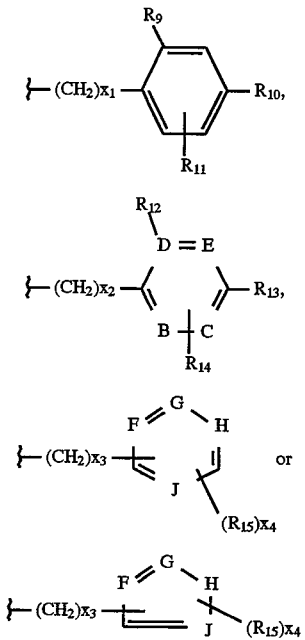

said $C_1$–$C_{20}$ alkyl and $C_1$–$C_{20}$ alkenyl group being optionally substituted with one or more $C_1$–$C_{20}$ alkyl groups;

$X_1$, $X_2$, $X_3$ and $X_4$ are independently 0–6;

$R_9$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —$NO_2$, —$NH_2$, —OH, —SH, —CHO and —COOH;

$R_{10}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —$NO_2$, —$NH_2$, —OH, —SH, —CHO, —COOH, —$NR_{16}R_{17}$, —$OR_{18}$, —$SR_{19}$, —$COOR_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl and thiopheneyl groups being optionally substituted with one or more halogen, —$OCH_3$ or $C_1$–$C_6$ alkyl groups;

$R_{11}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —$NO_2$, —$NH_2$, —OH, —SH, —CHO, —COOH, —$NR_{16}R_{17}$, —$OR_{18}$, —$SR_{19}$, —$COOR_{20}$, phenyl, pyridyl, pyrazinyl, imidazolyl, pyrimidyl, triazyl, triazolyl, thiadiazolyl, tetrazolyl, thiazolyl, thiadiazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl and thiopheneyl groups being optionally substituted with one or more halogen, —$OCH_3$ or $C_1$–$C_6$ alkyl groups;

$R_{12}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —$NO_2$, —$NH_2$, —OH, —SH, —CHO and —COOH;

$R_{13}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —$NO_2$, —$NH_2$, —OH, —SH, —CHO, —COOH, —$NR_{16}R_{17}$, —$OR_{18}$, —$SR_{19}$, —$COOR_{20}$, phenyl, pyridyl, pyrazinyl, imidazolyl, pyrimidyl, triazyl, triazolyl, thiadiazolyl, tetrazolyl, thiazolyl, thiadiazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl and thiopheneyl groups being optionally substituted with one or more halogen, —$OCH_3$ or $C_1$–$C_6$ alkyl groups;

$R_{14}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —$NO_2$, —$NH_2$, —OH, —SH, —CHO, —COOH, —$NR_{16}R_{17}$, —$OR_{18}$, —$SR_{19}$, —$COOR_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl and thiopheneyl groups being optionally substituted with one or more halogen, —$OCH_3$ or $C_1$–$C_6$ alkyl groups;

$R_{15}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —$NO_2$, —$NH_2$, —OH, —SH, —CHO, —COOH, —$COOR_{25}$, and phenyl; said phenyl being optionally substituted with one or more halogens, —$OCH_3$ or $C_1$–$C_6$ alkyl groups;

$R_{16}$ and $R_{17}$ are independently a $C_1$–$C_6$ alkyl group or form together a ring of 3 to 8 carbon atoms;

$R_{18}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, an alkyl acyl radical comprising 2 to 6 carbon atoms, and a phenyl acyl radical; said phenyl being optionally substituted with one or more halogens, —$OCH_3$ or $C_1$–$C_6$ alkyl groups;

$R_{19}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, an alkyl acyl radical comprising 2 to 6 carbon atoms, and a phenyl acyl radical; said phenyl being optionally substituted with one or more halogens, —$OCH_3$ or $C_1$–$C_6$ alkyl groups;

$R_{20}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, and a benzyl group; said phenyl and benzyl groups being optionally substituted with one or more halogens, —$OCH_3$ or $C_1$–$C_6$ alkyl groups;

$R_{21}$ and $R_{22}$ are independently $C_1$–$C_6$ alkyl groups or form together a ring of 3 to 8 carbon atoms;

$R_{23}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, an alkyl acyl radical comprising 2 to 6 carbon atoms, and a phenyl acyl radical; said phenyl being optionally substituted with one or more halogens, —$OCH_3$ or $C_1$–$C_6$ alkyl groups;

$R_{24}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, an alkyl acyl radical comprising 2 to 6 carbon atoms, and a phenyl acyl radical; said phenyl being optionally substituted with one or more halogens, -$OCH_3$ or $C_1$–$C_6$ alkyl groups;

$R_{25}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, and a benzyl group; said phenyl and benzyl groups being optionally substituted with one or more halogens, —$OCH_3$ or $C_1$–$C_6$ alkyl groups;

B, C, D, and E are independently carbon or nitrogen;

F, G, H, and J are independently selected from the group consisting of carbon, nitrogen and sulfur, and with the provisio that only one of either F, G, H, or J can be sulfur, and with the further provisio that if one of either F, G, H, or J is sulfur, then $R_{15}$ is hydrogen or $x_4$=0.

The novel 1-2-dithiin compounds of formula I are useful as antifungal or anti-infective agents.

In a preferred embodiment, the invention provides novel 1,2-dithiin compounds having the formula II:

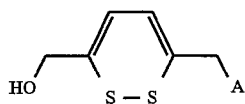

and pharmaceutically acceptable salts thereof, wherein:

A is selected from the group consisting of —OAr, —O(CO)Ar, —NH(CO)Ar, —S—Ar and B;

Ar is selected from the group consisting of phenyl, 1-imidazolyl, 2-imidazolyl, 3-imidazolyl, 4-imidazolyl, 5-imidazolyl, 2-pyridyl, 3-pyridyl, 4-pyridyl, 3-pyridazinyl, 4-pyridazinyl, 2-quinoxalinyl, 3-quinoxalinyl, 5-quinoxalinyl, 6-quinoxalinyl, 7-quinoxalinyl, 8-quinoxalinyl and 5-tetrazolyl; said Ar being optionally substituted with one or more groups selected from the group consisting of phenyl, —OH, —OR, —COOH, —N(R)(R), —F, —Cl, —Br, —I, —$CF_3$, —$CCl_3$, —$CBr_3$, —$CI_3$, —$NO_2$, a $C_1$–$C_{10}$ alkyl group, a $C_2$–$C_{10}$ alkenyl group, a $C_2$–$C_{10}$ alkynyl group, —C(O)O$C_1$–$C_{10}$ alkyl group, —C(O)O$C_2$–$C_{10}$ alkenyl group, —C(O)O$C_2$–$C_{10}$ alkynyl group and B;

each R is independently selected from the group consisting of H, a $C_1$–$C_{10}$ alkyl group, a $C_2$–$C_{10}$ alkenyl group and a $C_2$–$C_{10}$ alkynyl group; and B is a 5–7 membered saturated or unsaturated carbocyclic ring optionally having one or more heteroatoms selected from the group consisting of O, S and N; said B being optionally substituted with one or more groups selected from the group consisting of —OH, —OR, —COOH, —N(R)(R), —F, —Cl, —Br, —I, —$CF_3$, —$CCl_3$, —$CBr_3$, —$CI_3$, —$NO_2$, a $C_1$–$C_{10}$ alkyl group, a $C_2$–$C_{10}$ alkenyl group, a $C_2$–$C_{10}$ alkynyl group, —C(O)O$C_1$–$C_{10}$ alkyl group, —C(O)O$C_2$–$C_{10}$ alkenyl group, —C(O)O$C_2$–$C_{10}$ alkynyl group and =O.

The novel 1,2-dithiin compounds of formula II are useful as antifungal or anti-infective agents.

Especially preferred compounds of formula II useful as antifungal or anti-infective agents are:

3-(hydroxymethyl)-6-[(phenyloxy)methyl]-1,2-dithiin;

3-(hydroxymethyl)-6-[(pyridyl-2-oxy)methyl]-1,2-dithiin;

3-(hydroxymethyl)-6-[(pyrid-2-one-1-yl)methyl]-1,2-dithiin;

3-(hydroxymethyl)-6-[(pyridyl-3-oxy)methyl]-1,2-dithiin;

3-(hydroxymethyl)-6-[(3-hydroxyphenyloxy)methyl]-1,2-dithiin;

3-(hydroxymethyl)-6-[[3-(N,N-dimethylamino)-phenyloxy]methyl]-1,2-dithiin;

3-(hydroxymethyl)-6-[(3-hydroxypyridazin-6-one-1-yl)methyl]-1,2-dithiin;

3-(hydroxymethyl)-6-[(3-hydroxypyridazine-6-oxy)methyl]-1,2-dithiin;

3-(hydroxymethyl)-6-[(2-trifluoromethylphenyloxy)methyl]-1,2-dithiin;

3-(hydroxymethyl)-6-[(2-fluorophenyloxy)methyl]-1,2-dithiin;

3-(hydroxymethyl)-6-[(5-nitropyridyl-2-oxy)methyl]-1,2-dithiin;

3-(hydroxymethyl)-6-[(5-nitropyrid-2-one-1-yl)methyl]-1,2-dithiin;

3-(hydroxymethyl)-6-[(3-ethynylphenyloxy)methyl]-1,2-dithiin;

3-(hydroxymethyl)-6-[methyloxy[methylbenzoate-3-yl]]-1,2-dithiin;

3-(hydroxymethyl)-6-[methyloxy[3-hydroxyquinoxalin-2-yl]]-1,2-dithiin;

3-(hydroxymethyl)-6-[(2-chloro-5-trifluoromethylphenyloxy)methyl]-1,2-dithiin;

3-(hydroxymethyl)-6-[methyloxy[methyl benzoate-4-yl]]-1,2-dithiin;

3-(hydroxymethyl)-6-[(2-hydroxy-3-fluorophenyloxy-1-yl)methyl]-1,2-dithiin;

3-(hydroxymethyl)-6-[(1-hydroxy-3-fluorophenyloxy-2-yl)methyl]-1,2-dithiin;

3-(hydroxymethyl)-6-[methylthio-[1-(4-hydroxyphenyl)tetrazol-5-yl]-1,2-dithiin;

3-(hydroxymethyl)-6-[[4-(imidazol-1-yl)phenyloxy]methyl]-1,2-dithiin;

3-(hydroxymethyl)-6-[[(2,2-dimethyl-1,3-dioxolan-4-yl)methyloxy]methyl]-1,2-dithiin;

3,6-bis{[(2,2-dimethyl-1,3-dioxolan-4-yl)methyloxy]methyl}-1,2-dithiin;

3-(hydroxymethyl)-6-[methyloxy(2,3-dihydroxypropane-1-yl)]-1,2-dithiin;

3-[[(2,2-dimethyl-1,3-dioxolan-4-yl)methyloxy]methyl]-6-[[methyloxy(2,3-dihydroxypropane-1-yl)]]-1,2-dithiin;

3-(hydroxymethyl)-6-[methyloxy[methyl benzoate-2-yl]]-1,2-dithiin; and 3-(benzoyloxymethyl)-6-(hydroxymethyl)-1,2-dithiin.

The present invention may be understood more fully by reference to the following figures, detailed description and illustrative examples which are intended to exemplify non-limiting embodiments of the invention.

DETAILED DESCRIPTION OF THE INVENTION

SYNTHESIS OF THE 1,2-DITHIIN COMPOUNDS

The 1,2-dithiin compounds described in this invention can be prepared by synthetic methods outlined below. The precursors 6-[(tert-butyldimethylsilyloxy)methyl]-3-(hydroxymethyl)-1,2-dithiin and 3,6-[bis(hydroxymethyl)]-1,2-dithiin are prepared as previously described in U.S. Ser. No. 08/212,096, herein incorporated by reference, and in Koreeda and Yang (Synlett, 1994, 201).

Figure 1:
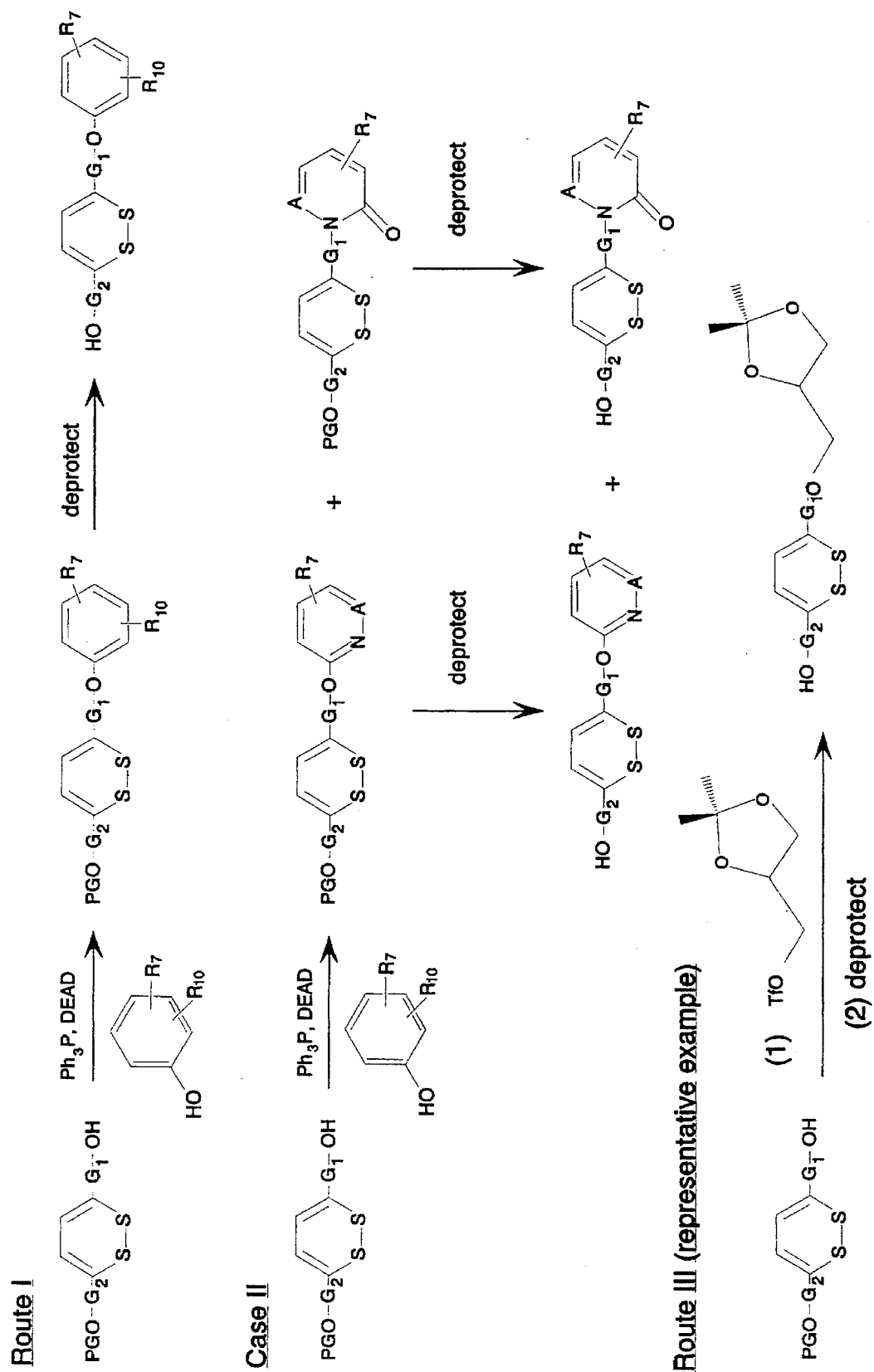
FIG. 1 is a flow-chart describing the synthesis of the 1,2-dithiins of formula I. $Tf=CF_3S(O)_2O^-$; DEAD=diethylazodicarboxylate; PG=protecting group.

As shown in FIG. 1, compounds of formula I can be obtained via Routes I, II or III.

For example, compounds of formula I which bear a benzene ether appended to $G_1$, wherein $G_1$ is defined as above for compounds of formula I, can be prepared by etherifying a mono-protected 1,2-dithiin alcohol with an $R_7$- and/or $R_{10}$-substituted phenol, wherein $R_7$ and $R_{10}$ is defined above for compounds of formula I (Route I). Such protecting groups useful are those described in "Protective Groups in Organic Synthesis", T. W. Greene, John Wiley & Sons, New York, 1981. Preferably, the protecting group is the tert-butyldimethylsilyl protecting group. The mono-protected 1,2-dithiin alcohol is then etherified with the $R_7$- and/or $R_{10}$-substituted phenol in the presence of a reagent which is capable of activating the —OH group of the mono-protected 1,2-dithiin alcohol so that its leaving group ability is enhanced. Such reagents to be used in this regard include, but are not limited to diethylazodicarboxylate or diisopropylazodicarboxylate and triphenylphosphine or tributylphosphine. Preferably, diethylazodicarboxylate (DEAD) and triphenylphosphine are used. The resulting $R_7$- and/or $R_{10}$-substituted 1,2-dithiin ether is subsequently deprotected (i.e., "PG" removed) using those methods described by T. W. Greene, as above, for the particular protecting group chosen. When the tert-butyldimethylsilyl protecting group is used, treatment with tetrabutylammonium fluoride or hydrogen fluoride are the preferred methods of deprotection. Most preferably, the tetrabutylammonium fluoride is used in conjunction with acetic acid or hydrogen fluoride in aqueous acetonitrile is used.

In Route II, compounds which bear a pyridine or pyridazine ether appended to $G_1$, wherein $G_1$ is defined as above for compounds of formula I, can be similarly prepared by etherifying the mono-protected 1,2-dithiin alcohol with an $R_7$-substituted hydroxypyridine or $R_7$-substituted hydroxypyridazine, using the methods described above for the synthesis of 1,2-dithiins having benzene ether groups. Preferably, the protecting group is a tert-butyldimethylsilyl protecting group and the reagent used to enhance the leaving group ability of the —OH group of the mono-protected 1,2-dithiin alcohol is DEAD.

The reaction between the mono-protected 1,2-dithiin alcohol with the $R_7$-substituted hydroxypyridine or hydroxypyridazine can also yield a mono-protected 1,2-dithiin bearing an $R_7$-substituted pyridone or pyridazone linked to the 1,2-dithiin via $G_1$, wherein $G_1$ is defined as above for the compounds of formula I, and the pyridone nitrogen or the pyridazone 1-nitrogen (Route II). The resulting mono-protected 1,2-dithiin bearing such pyridone or pyridazone is deprotected, using the methods described above to give a pyridone- or pyridazone-substituted 1,2-dithiin alcohol. Preferably, the protecting group is the tert-butyldimethylsilyl protecting group and the reagent used for deprotection is tetrabutylammonium fluoride, preferably in the presence of acetic acid.

Monoprotected 1,2-dithiin alcohols of the present invention can further be etherified via treatment with compounds activated with leaving groups, so that upon treatment with such compounds, a C-O bond will be formed between the carbon bearing the leaving group and the —OH group of the mono-protected 1,2-dithiin alcohol, with concommitment departure of the leaving group (ROUTE III). Such suitable leaving groups include, but are not limited to halide, p-toluenesulfonate, p-nitrobenzene sulfonate, p-halo benzenesulfonate, benzenesulfonate, trifluoromethane sulfonate and acetate. Preferably, the leaving group is a trifluoromethanesulfonate (TfO—) leaving group. The resulting ether is then deprotected, by methods described above, to yield 1,2-dithiin ethers of formula I. Preferably, the protecting group is the tert-butyldimethysilyl protecting group and the reagent used for deprotection is tetrabutylammonium fluoride, preferably in the presence of acetic acid.

Figure 2:
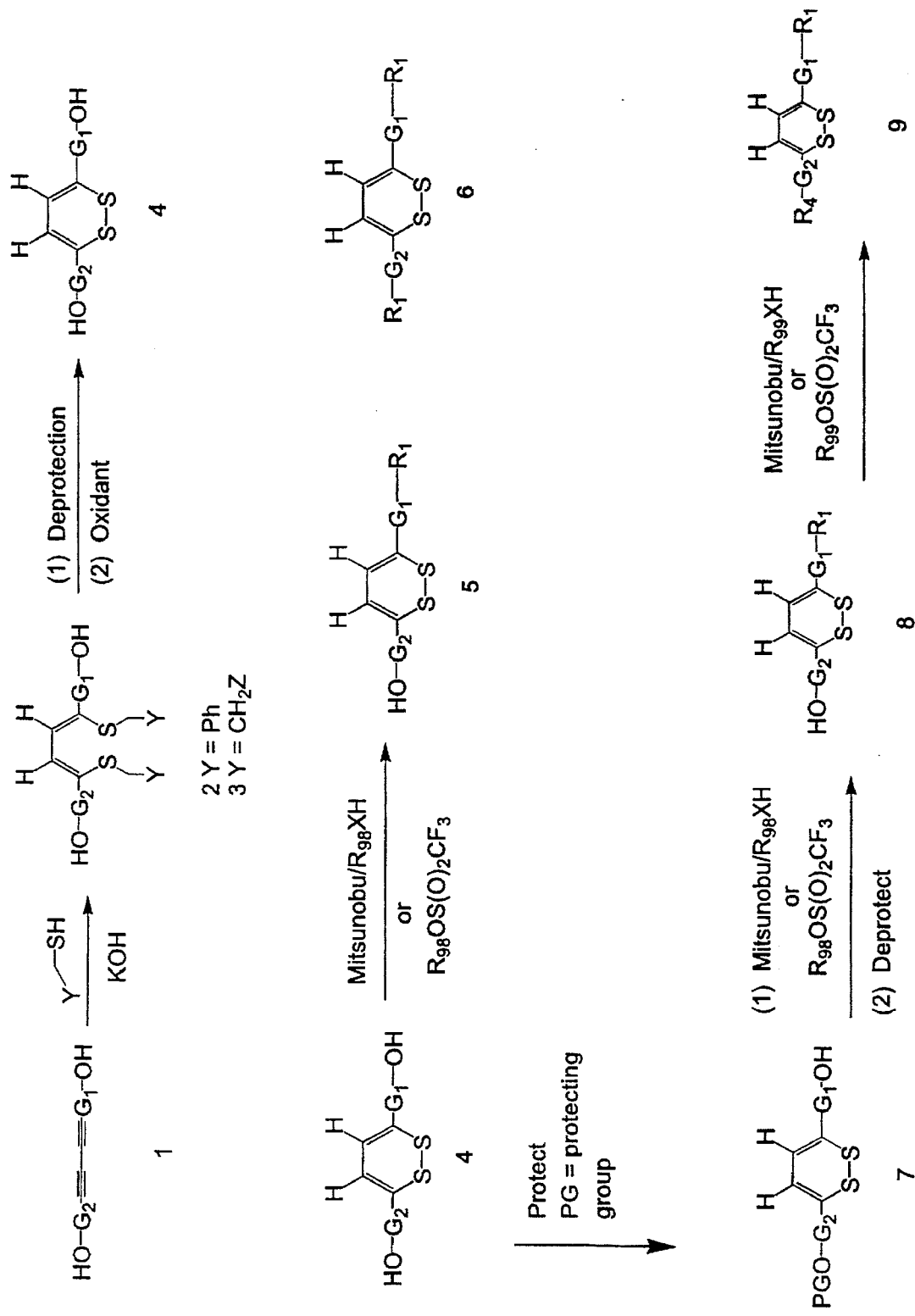
FIG. 2 is a flow-chart describing a further embodiment of the synthesis of the 1,2-dithiins of formula I. $R_1H$ and $R_4H=R_{98}XH$ and $R_{99}XH$, respectively, where X=sulfur or oxygen.

FIG. 2 shows how compounds of formula I can be prepared from dialkyne 1 by bis-addition of benzyl mercaptan to yield diene adduct 2 (Y=Ph) according to the procedure of Koreeda and Yang [Koreeda, M.; Yang, W. Synlett 1994, 201] Truong et al. Diene 2 is then deprotected using sodium in liquid ammonia and the subsequent dithiolate anion is oxidized with an oxidizing agent, preferably $K_3Fe(CN)_6$ or $KI/I_2$, to give dithiin 4 [Koreeda and Wang *Syniett* 1994, 201]. Alternatively, dialkyne 1 can be treated with $YCH_2SH$, where Y can be among $CH_2CN$, $CH_2NO_2$, $CH_2COOCH_3$, but preferably $CH_2CN$, to yield diene adduct 3 according to the procedure of Truong et al. [Bierer, D. E, Dener, J. M.; Truong, T. V. U.S. patent application Ser. No. 08/212,096]. Diene 3 is then deprotected using a base such as potassium tert-butoxide and the subsequent dithiolate anion is oxidized with an oxidizing agent, preferably $K_3Fe(CN)_6$ or $KI/I_2$ to give dithiin 4 [Truong et al U.S. patent application Ser. No. 08/212,096]. Dithiin 4 can then be treated under Mitsunobu conditions [Hughes, D. L. *Org. Reactions* 1992, 42, 335–636; Mitsunobu, O. *Synthesis* 1981, 1–28, with $R_{98}XH$ to dithiins 5 and/or 6, the product ratio being dependent on the stoichiometry of the reaction conditions. Alkyl ether dithiins 5 and 6 can be prepared by reaction of dithiin 4 with $R_{98}OS(O)_2CF_3$, the product ratio being dependent on the reaction stoichiometry. Alternatively, dithiin 4 can be protected with a protecting group [Theodore Green and Peter G. M. Wuts *Protective*

Groups in Organic Synthesis; John Wiley & Sons, Inc.; New York, 1991], preferably a silyl protecting group such as tert-butyldimethylsilyl, to afford dithiin 7. Dithiin 7 is then treated under Mitsunobu conditions or alkylated with $R_{98}OS(O)_2CF_3$ to provide, following deprotection, dithiin 8. Dithiin 8 can optionally be subjected to Mitsunobu reaction with $R_{99}XH$ or alkylated with $R_{99}OS(O)_2CF_3$ to give dithiin 9. Compound 2 and compound 4 can be prepared by procedure of Koreeda and Wang Synlett 1994, 201. Compound 3, where $Z=CH_2CN$, $CH_2NO_2$, $CH_2COOR$, etc., and compound 4 can be prepared according to Truong et al., U.S. Ser. No. 08/212,096.

Figure 3:
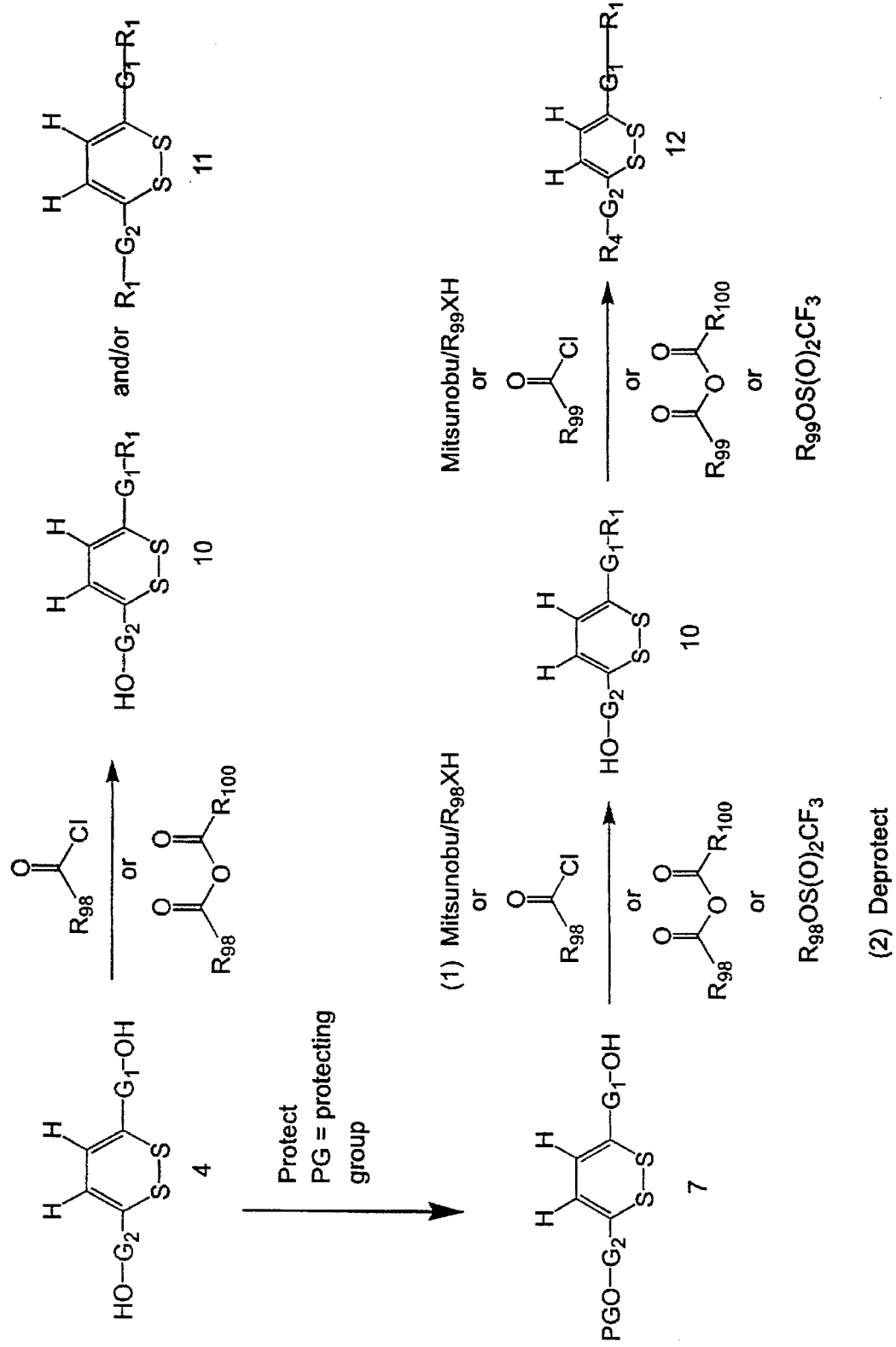
FIG. 3 is a flow-chart describing a still further embodiment of the synthesis of the 1,2-dithiins of formula I. $R_1H$ and $R_4H=R_{98}XH$ and $R_{99}XH$, respectively, where X=sulfur or oxygen. $R_1$ further comprises $R_{98}(C=O)$. $R_4$ further comprises $R_{99}(C=O)$. $R_{100}=R_{98}$, $R_{99}$, $C_1-C_{10}$ alkyl or phenyl.

FIG. 3 shows how compounds of formula I can further be made by acylation of dithiin 4 with an acid halide, an acid anhydride, or a mixed acid anhydride, to afford dithiins 10 and/or 11, the product ratio being dependent on the reaction stoichiometry. Alternatively, dithiin 7 can be acylated, alkylated with $R_{98}OS(O)_2CF_3$, or subjected to Mitsunobu conditions with $R_{98}XH$ to provide dithiin 10. Dithiin 10 can optionally be subjected to Mitsunobu reaction with $R_{99}XH$, alkylated with $R_{99}OS(O)_2CF_3$, or acylated with an acid halide, an acid anhydride, or a mixed acid anhydride, to give dithiin 12.

Figure 4:
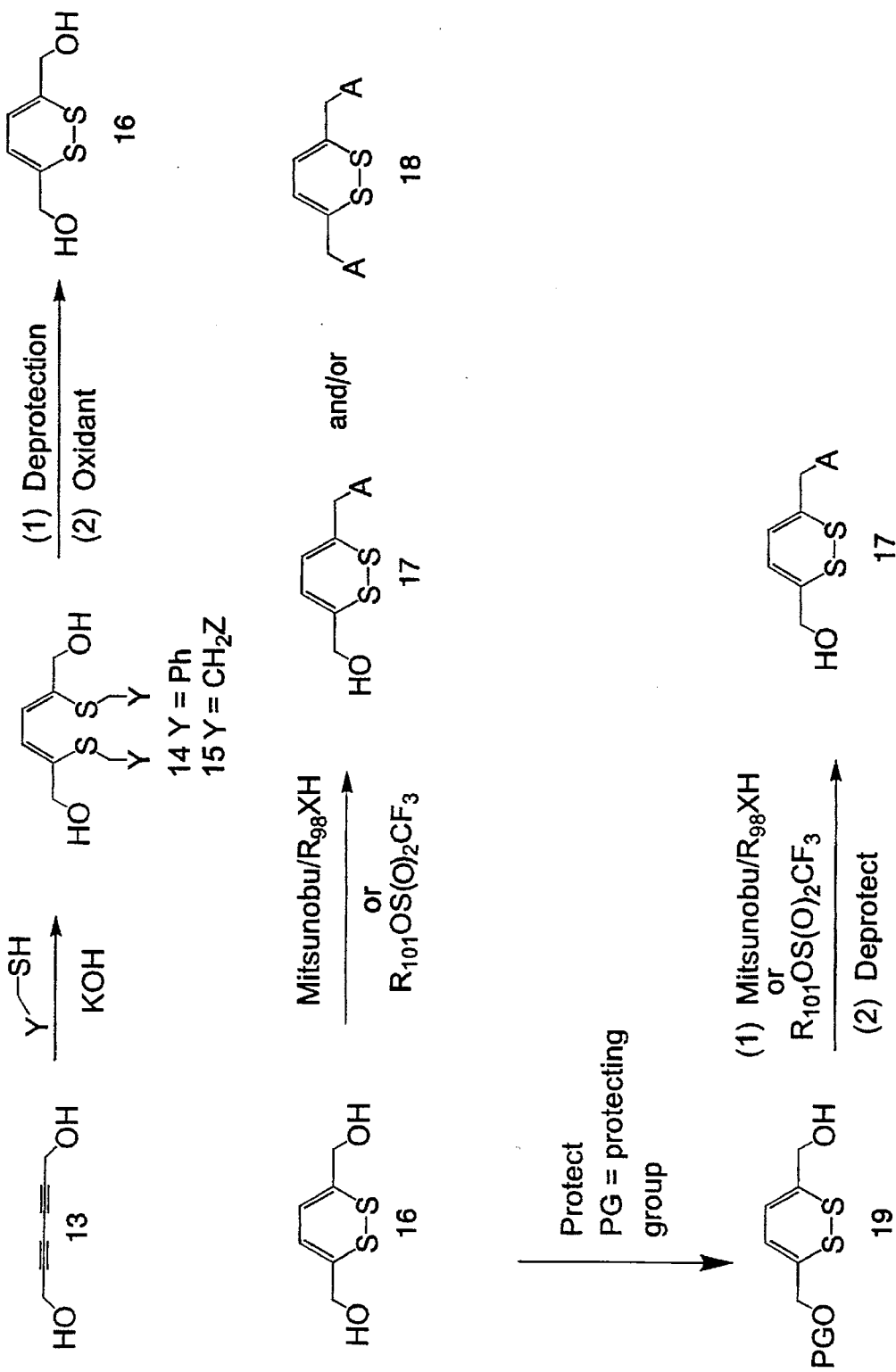
FIG. 4 is a flow-chart describing the synthesis of the 1,2-dithiins of formula II. $A=R_{101}XH$, where X=sulfur or oxygen.

FIG. 4 shows how compounds of formula II can be prepared from 2,4-hexadiyne-1, 6-diol 13 by bis-addition of benzyl mercaptan to yield diene adduct 14 (Y=Ph) according to the procedure of Koreeda and Yang [Koreeda, M.; Yang, W. Synlett 1994,201]. Diene 14 is then deprotected using sodium in liquid ammonia and the subsequent dithiolate anion is oxidized with an oxidizing agent, preferably $K_3Fe(CN)_6$ or $KI/I_2$, to give dithiin 16 [Koreeda and Wang Synlett 1994, 201]. Alternatively, dialkyne 13 can be treated with $YCH_2SH$, where Y can be among $CH_2CN$, $CH_2NO_2$, $CH_2COOCH_3$, but preferably $CH_2CN$, to yield diene adduct 15 according to the procedure of Truong et al [Bierer, D. E, Dener, J. M.; Truong, T. V. U.S. patent application Ser. No. 08/212,096]. Diene 15 is then deprotected using a base such as potassium tertbutoxide and the subsequent dithiolate anion is oxidized with an oxidizing agent, preferably $K_3Fe(CN)_6$ or $KI/I_2$ to give dithiin 16 [Truong et al U.S. patent application Ser. No. 08/212,096]. Dithiin 16 can then be treated under Mitsunobu conditions [Hughes, D. L Org. Reactions 1992, 42, 335–636; Netsunobu, O. Synthesis 1981, 1–28] with $R_{101}XH$ to dithiins 17 and/or 18, the product ratio being dependent on the stoichiometry of the reaction conditions. Alkyl ether dithiins 17 and 18 can be prepared by reaction of dithiin 16 with $R_{101}OS(O)_2CF_3$, the product ratio being dependent on the reaction stoichiometry. Alternatively, dithiin 16 can be protected with a protecting group [Theodora Green and Peter G. M. Wuts Protective Groups in Organic Synthesis; John Wiley & Sons, Inc.; New York, 1991], preferably a silyl protecting group such as tert-butyldimethylsilyl, to afford dithiin 19. Dithiin 19 is then treated under Mitsunobu conditions or alkylated with $R_{101}OS(O)_2CF_3$ to provide, following deprotection, dithiin 17. Compound 14 and compound 16 can be prepared by procedure of Koreeda and Wang Synlett 1994, 201. Compound 15, where $Z=CH_2CN$, $CH_2NO_2$, $CH_2COOR$, etc., and compound 16 can be prepared according to Truong et al., U.S. Ser. No. 08/212,096.

Figure 5:
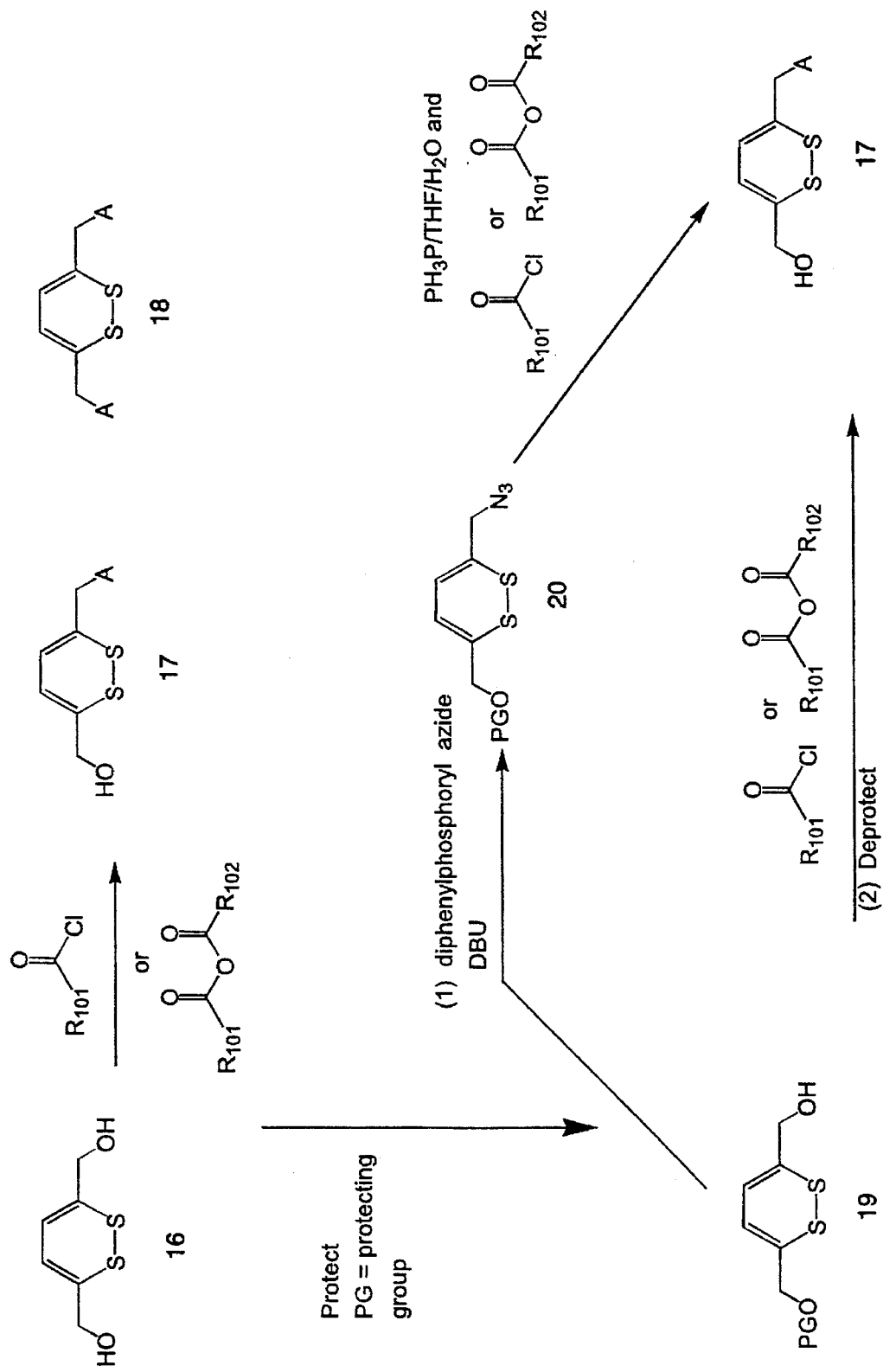
FIG. 5 is a flow-chart describing a further embodiment of the synthesis of the 1,2-dithiins of formula II. $A=R_{101}XH$, where X=sulfur or oxygen; $R_{101}(C=O)$; $R_{101}(C=O)NH$; or $N_3$. $R_{102}=R_{101}$, $C_1-C_{10}$ alkyl or phenyl.

FIG. 5 shows how compounds of Formula II can further be made by acylation of dithiin 16 with an acid halide an acid anhydride, or a mixed acid anhydride, to afford dithiins 17 and/or 18, the product ratio being dependent on the reaction stoichiometry. Alternatively, dithiin 19 can be acylated to provide, following deprotection, dithiin 17. Amides 17 can be prepared from azide 20, which is prepared from dithiin 19 upon reaction with diphenylphosphorylazide in the presence of DBU [Truong et al. U.S. patent application Ser. No. 08/212,096]. Reduction of azide 20 with $PH_3P/THF/H_2O$ in the presence of an acid halide, acid anhydride, or mixed acid anhydride provides amide 17. The reaction of 19 with diphenylphosphorylazide and DBU to form the intermediate azide can be prepared according to Truong et al., U.S. Ser. No. 08/212,096. The synthesis of amides 17 is also described therein.

METHODS FOR USE OF 1,2-DITHIIN COMPOUNDS

Due to the potent activities of the presently described 1,2-dithiin compounds, the 1,2-dithiin compounds of the present invention are useful as antifungal or anti-infective agents in veterinary and human medicine against a wide range of pathogens. Fungal species which are inhibited by the 1,2-dithiin compounds of the present invention include, but are not limited to, Candida albicans, Cryptococcus neoformans, Aspergillus fumigatus, Candida krusei, Candida parapsilosis, Candida tropicalis, Trichophyton rubrum, Epidermophyton species, Microsporum species, Sporothrix species, Blastomyces dermatitidis, Coccidiodes immiitis, and Histoplasma capsulatum. Viruses which are inhibited by the 1,2-dithiin compounds of the present invention include Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdovirus, Togavirus, and Hepadnavirus. Bacteria which are inhibited by the 1,2-dithiin compounds include Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens, Listeria, Monocytogenes, Enterococcus faecalis, Streptococcus pyogenes; Streptococcus pneumonia, Viridans streptococci, Haemophilus influenzae, Proteus mirabilis, Proteus vulgaris and Bacterioides fragilis.

Additionally, the 1,2-dithiin compounds of the present invention are useful as an active agent in an antiseptic, disinfectant or cleaning composition which has fungicidal and/or fungistatic, and/or anti-bacterial and/or anti-viral properties. According to this embodiment of the invention, the novel 1,2-dithiins are used to retard or inhibit fungal and/or bacterial growth on surfaces of a variety of materials including, but not limited to animal, including human, skin, and surfaces of inanimate objects used, for example, in homes or offices. The compounds may be used in such compositions either as the sole active agent or in combination with other active anti-fungal and/or anti-bacterial agents. In a specific illustrative example (see Section 6, infra), the compounds are used to inhibit fungal growth, for example, on laboratory glassware or on bathroom surfaces.

When administered to a mammal for veterinary use or to a human for clinical use, the 1,2-dithiin compounds can be used alone or may be combined with any physiologically acceptable carrier such as water, an aqueous solution, normal saline, or any other physiologically accetable excipient. In general, the dosage would range from about 0.1–500 mg/kg/day, preferably about 1–100 mg/kg/day.

The 1,2-dithiin compounds can be administered by a number of routes including, but not limited to: orally; topically; nasally; parenterally; by aerosol; by injection including, but not limited to intraperitoneally, subcutaneously, intramuscularly, etc.; and combinations thereof. The preferred route of administration is oral.

According to an embodiment of the invention, pharmaceutical compositions comprising the novel 1,2-dithiin compounds having the structure of formula I:

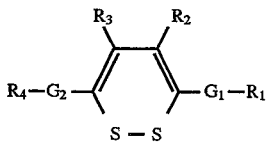

and pharmaceutically acceptable salts thereof, wherein:

$R_2$ and $R_3$ are hydrogen;

$G_1$ and $G_2$ are independently selected from the group consisting of a $C_1$–$C_{10}$ alkyl or branched alkyl group and a $C_3$–$C_{10}$ cycloalkyl group;

$R_1$ and $R_4$ are independently selected from the group consisting of hydrogen, —OH, —OH$_5$, —O(CO)R$_5$, —SR$_6$ or a pyridone radical of the type:

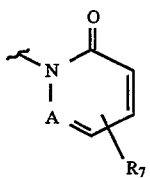

wherein $R_7$ is selected from the group consisting of hydrogen, —OH, —SH, —NO$_2$, —NH$_2$, halogen, trifluoromethyl, —CHO, —COOH, —COOR$_8$, —OR$_8$ and SR$_8$;

A is nitrogen or carbon;

$R_8$ is an alkyl group of 1 to 6 carbon atoms;

$R_5$ and $R_6$ are independently selected from the group consisting of a $C_1$–$C_{20}$ alkyl group, a $C_1$–$C_{20}$ alkenyl group, a $C_3$–$C_{10}$ cycloalkyl group and a radical of the type:

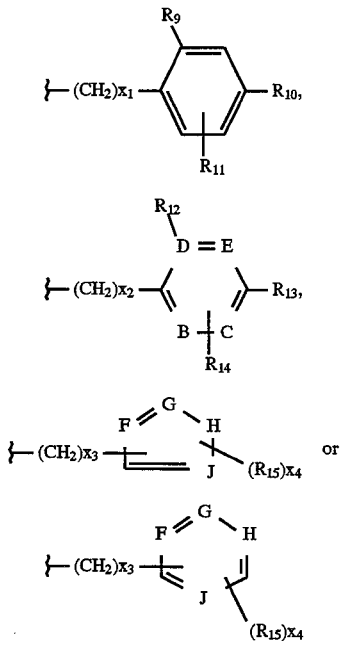

said $C_1$–$C_{20}$ alkyl and $C_1$–$C_{20}$ alkenyl group being optionally substituted with one or more $C_1$–$C_{20}$ alkyl groups;

$X_1$, $X_2$, $X_3$ and $X_4$ are independently 0–6;

$R_9$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —NO$_2$, —NH$_2$, —OH, —SH, —CHO and —COOH;

$R_{10}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —NO$_2$, —NH$_2$, —OH, —SH, —CHO, —COOH, —NR$_{16}$R$_{17}$, —OR$_{18}$, —SR$_{19}$, —COOR$_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl and thiopheneyl groups being optionally substituted with one or more halogen, —OCH$_3$ or $C_1$–$C_6$ alkyl groups;

$R_{11}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —NO$_2$, —NH$_2$, —OH, —SH, —CHO, —COOH, —NR$_{16}$R$_{17}$, —OR$_{18}$, —SR$_{19}$, —COOR$_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl and thiopheneyl groups being optionally substituted with one or more halogen, —OCH$_3$ or $C_1$–$C_6$ alkyl groups;

$R_{12}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —NO$_2$, —NH$_2$, —OH, —SH, —CHO and —COOH;

$R_{13}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —NO$_2$, —NH$_2$, —OH, —SH, —CHO, —COOH, —NR$_{16}$R$_{17}$, —OR$_{18}$, —SR$_{19}$, —COOR$_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl and thiopheneyl groups being optionally substituted with one or more halogen, —OCH$_3$ or $C_1$–$C_6$ alkyl groups;

$R_{14}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —NO$_2$, —NH$_2$, —OH, —SH, —CHO, —COOH, —NR$_{16}$R$_{17}$, —OR$_{18}$, —SR$_{19}$, —COOR$_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl and thiopheneyl groups being optionally substituted with one or more halogen, —OCH$_3$ or $C_1$–$C_6$ alkyl groups;

$R_{15}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —NO$_2$, —NH$_2$, —OH, —SH, —CHO, —COOH, —COOR$_{25}$, and phenyl; said phenyl being optionally substituted with one or more halogens, —OCH$_3$ or $C_1$–$C_6$ alkyl groups;

$R_{16}$ and $R_{17}$ are independently a $C_1$–$C_6$ alkyl group or form together a ring of 3 to 8 carbon atoms;

$R_{18}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, an alkyl acyl radical comprising 2 to 6 carbon atoms, and a phenyl acyl radical; said phenyl being optionally substituted with one or more halogens, —OCH$_3$ or C$_1$–C$_6$ alkyl groups;

R$_{19}$ is selected from the group consisting of a C$_1$–C$_6$ alkyl group, a C$_2$–C$_6$ alkenyl group, a C$_2$–C$_6$ alkynyl group, a C$_3$–C$_8$ cycloalkyl group, a phenyl group, an alkyl acyl radical comprising 2 to 6 carbon atoms, and a phenyl acyl radical; said phenyl being optionally substituted with one or more halogens, —OCH$_3$ or C$_1$–C$_6$ alkyl groups;

R$_{20}$ is selected from the group consisting of a C$_1$–C$_6$ alkyl group, a C$_2$–C$_6$ alkenyl group, a C$_2$–C$_6$ alkynyl group, a C$_3$–C$_8$ cycloalkyl group, a phenyl group, and a benzyl group; said phenyl and benzyl groups being optionally substituted with one or more halogens, —OCH$_3$ or C$_1$–C$_6$ alkyl groups;

R$_{21}$ and R$_{22}$ are independently C$_1$–C$_6$ alkyl groups or form together a ring of 3 to 8 carbon atoms;

R$_{23}$ is selected from the group consisting of a C$_1$–C$_6$ alkyl group, a C$_2$–C$_6$ alkenyl group, a C$_2$–C$_6$ alkynyl group, a C$_3$–C$_8$ cycloalkyl group, a phenyl group, an alkyl acyl radical comprising 2 to 6 carbon atoms, and a phenyl acyl radical; said phenyl being optionally substituted with one or more halogens, —OCH$_3$ or C$_1$–C$_6$ alkyl groups;

R$_{24}$ is selected from the group consisting of a C$_1$–C$_6$ alkyl group, a C$_2$–C$_6$ alkenyl group, a C$_2$–C$_6$ alkynyl group, a C$_3$–C$_8$ cycloalkyl group, a phenyl group, an alkyl acyl radical comprising 2 to 6 carbon atoms, and a phenyl acyl radical; said phenyl being optionally substituted with one or more halogens, —OCH$_3$ or C$_1$–C$_6$ alkyl groups;

R$_{25}$ is selected from the group consisting of a C$_1$–C$_6$ alkyl group, a C$_2$–C$_6$ alkenyl group, a C$_2$–C$_6$ alkynyl group, a C$_3$–C$_8$ cycloalkyl group, a phenyl group, and a benzyl group; said phenyl and benzyl groups being optionally substituted with one or more halogens, —OCH$_3$ or C$_1$–C$_6$ alkyl groups;

B, C, D, and E are independently carbon or nitrogen;

F, G, H, and J are independently selected from the group consisting of carbon, nitrogen and sulfur, and with the proviso that only one of either F, G, H, or J can be sulfur, and with the further provisio that if one of either F, G, H, or J is sulfur, then R$_{15}$ is hydrogen or x$_4$=0 are advantageously useful in veterinary or human medicine as antifungal or anti-infective agents.

According to a preferred embodiment, the invention provides pharmaceutical compositions comprising the novel 1,2-dithiin compounds having the formula II:

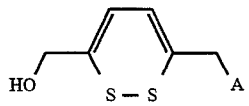

and pharmaceutically acceptable salts thereof, wherein:

A is selected from the group consisting of —OAr, —O(CO)Ar, —NH(CO)Ar, —S—Ar and B;

Ar is selected from the group consisting of phenyl, 1-imidazolyl, 2-imidazolyl, 3-imidazolyl, 4-imidazolyl, 5-imidazolyl, 2-pyridyl, 3-pyridyl, 4-pyridyl, 3-pyridazinyl, 4-pyridazinyl, 2-quinoxalinyl, 3-quinoxalinyl, 5-quinoxalinyl, 6-quinoxalinyl, 7-quinoxalinyl, 8-quinoxalinyl and 5-tetrazolyl; said Ar being optionally substituted with one or more groups selected from the group consisting of phenyl, —OH, —OR, —COOH, —N(R)(R), —F, —Cl, —Br, —I, —CF$_3$, —CCl$_3$, —CBr$_3$, —CI$_3$, —NO$_2$, a C$_1$–C$_{10}$ alkyl group, a C$_2$–C$_{10}$ alkenyl group, a C$_2$–C$_{10}$ alkynyl group, —C(O)OC$_1$–C$_{10}$ alkyl group, —C(O)OC$_2$–C$_{10}$ alkenyl group, —C(O)OC$_2$–C$_{10}$ alkynyl group and B;

each R is independently selected from the group consisting of H, a C$_1$–C$_{10}$ alkyl group, a C$_2$–C$_{10}$ alkenyl group and a C$_2$–C$_{10}$ alkynyl group; and B is a 5–7 membered saturated or unsaturated carbocyclic ring optionally having one or more heteroatoms selected from the group consisting of O, S and N; said B being optionally substituted with one or more groups selected from the group consisting of —OH, —OR, —COOH, —N(R)(R), —F, —Cl, —Br, —I, —CF$_3$, —CCl$_3$, —CBr$_3$, —CI$_3$, —NO$_2$, a C$_1$–C$_{10}$ alkyl group, a C$_2$–C$_{10}$ alkenyl group, a C$_2$–C$_{10}$ alkynyl group, —C(O)OC$_1$–C$_{10}$ alkyl group, —C(O)OC$_2$–C$_{10}$ alkenyl group, —C(O)OC$_2$–C$_{10}$ alkynyl group and =O are advantageously useful in veterinary or human medicine as antifungal or anti-infective agents.

A preferred mode of this embodiment of the invention encompasses pharmaceutical compositions comprising compounds selected from the group consisting of:

3-(hydroxymethyl)-6-[(phenyloxy)methyl]-1,2-dithiin;

3-(hydroxymethyl)-6-[(pyridyl-2-oxy)methyl]-1,2-dithiin;

3-(hydroxymethyl)-6-[(pyrid-2-one-1-yl)methyl]-1,2-dithiin;

3-(hydroxymethyl)-6-[(pyridyl-3-oxy)methyl]-1,2-dithiin;

3-(hydroxymethyl)-6-[(3-hydroxyphenyloxy)methyl]-1,2-dithiin;

3-(hydroxymethyl)-6-[[3-(N,N-dimethylamino)-phenyloxy]methyl]-1,2-dithiin;

3-(hydroxymethyl)-6-[(3-hydroxypyridazin-6-one-1-yl)methyl]-1,2-dithiin;

3-(hydroxymethyl)-6-[(3-hydroxypyridazine-6-oxy)methyl]-1,2-dithiin;

3-(hydroxymethyl)-6-[(2-trifluoromethylphenyloxy)methyl]-1,2-dithiin;

3-(hydroxymethyl)-6-[(2-fluorophenyloxy)methyl]-1,2-dithiin;

3-(hydroxymethyl)-6-[(5-nitropyridyl-2-oxy)methyl]-1,2-dithiin;

3-(hydroxymethyl)-6-[(5-nitropyrid-2-one-1-yl)methyl]-1,2-dithiin;

3-(hydroxymethyl)-6-[(3-ethynylphenyloxy)methyl]-1,2-dithiin;

3-(hydroxymethyl)-6-[methyloxy[methylbenzoate-3-yl]]-1,2-dithiin;

3-(hydroxymethyl)-6-[methyloxy[3-hydroxyquinoxalin-2-yl]]-1,2-dithiin;

3-(hydroxymethyl)-6-[(2-chloro-5-trifluoromethylphenyloxy)methyl]-1,2-dithiin;

3-(hydroxymethyl)-6-[methyloxy[methyl benzoate-4-yl]]-1,2-dithiin;

3-(hydroxymethyl)-6-[(2-hydroxy-3-fluorophenyloxy-1-yl)methyl]-1,2-dithiin;

3-(hydroxymethyl)-6-[(1-hydroxy-3-fluorophenyloxy-2-yl)methyl]-1,2-dithiin;

3-(hydroxymethyl)-6-[methylthio-[1-(4-hydroxyphenyl)tetrazol-5-yl]-1,2-dithiin;

3-(hydroxymethyl)-6-[[4-(imidazol-1-yl)phenyloxy]methyl]-1,2-dithiin;

3-(hydroxymethyl)-6-[[(2,2-dimethyl-1,3-dioxolan-4-yl)methyloxy]methyl]-1,2-dithiin;

3,6-bis{[(2,2-dimethyl-1,3-dioxolan-4-yl)methyloxy]methyl}-1,2-dithiin;

3-(hydroxymethyl)-6-[methyloxy(2,3-dihydroxypropane-1-yl)]-1,2-dithiin;

3-[[(2,2-dimethyl-1,3-dioxolan-4-yl)methyloxy]methyl]-6-[[methyloxy(2,3-dihydroxypropane-1-yl)]]-1,2-dithiin;

3-(hydroxymethyl)-6-[methyloxy[methyl benzoate-2-yl]]-1,2-dithiin; and 3-(benzoyloxymethyl)-6-(hydroxymethyl)-1,2-dithiin and pharmaceutically acceptable salts thereof; as anti-fungal or anti-infective agents.

By "pharmaceutically acceptable" is meant compatible with other ingredients used in combination with the 1,2-dithiin compounds or compositions of the present invention and non-deleterious to the recipient.

Such pharmaceutically acceptable salts include, but are not limited to hydrochloride, hydrobromide, hydroiodide, phosphate, sulfate, acetate, succinate, ascorbate, tartrate, gluconate, benzoate, malate, citrate, sodium, potassium, ammonium and fumarate.

In general, the compositions are prepared by uniformly and intimately bringing into association the active ingredient (s) with a liquid carrier or finely divided solid carrier or both, and then if necessary shaping the product. By "active ingredient(s)" is meant one or more of the 1,2-dithiin compounds of the present invention.

Compositions of the present invention suitable for oral administration may be administered as discrete units such as capsules, cachers or tablets each containing a predetermined amount of the active ingredient(s); as a powder or granules; as a solution or a suspension in an aqueous liquid or a non-aqueous liquid; or as an oil-in-water liquid emulsion or a water-in-oil liquid emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent known to those skilled in the art. Molded tablets may be made by molding in a suitable machine a mixture of the powdered compound moistened with an inert liquid diluent. The tablets may optionally be coated or scored and may be formulated so as to provide slow or controlled release of the active ingredient(s) therein.

Formulations suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for topical administration to the skin may be administered as ointments, creams, gels, and pastes comprising the active ingredient(s) to be administered in a pharmaceutically acceptable carrier. A preferred topical delivery system is a transdermal patch containing the ingredient to be administered.

Compostions suitable for nasal administration wherein the carrier is a solid, include a coarse powder having a particle size, for example, in the range 20 to 500 microns which is administered in the manner in which snuff is taken, i.e. by rapid inhalation through the nasal passage from a container of the powder held close up to the nose. Suitable formulations for nasal administration wherein the carrier is a liquid, as for example a nasal spray or as nasal drops, include aqueous or oily solutions of the active ingredient(s).

Compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose containers, for example, sealed ampules and vials, and may be stored in a freeze-dried (lyophilized) condition requiring only the addition of a sterile liquid carrier, for example water for injections, immediately prior to use. Extemporous injection solutions and suspensions may be prepared from sterile powders, granules, and tablets of the kind described above.

Preferred unit dosage formulations are those containing a daily dose or unit, daily sub-dose, as recited above, or an appropriate fraction thereof, of the administered active ingredient(s).

It should be understood that in addition to the additives particularly mentioned above the compositions of this invention may include other agents conventional in the art having regard to the type of composition in question, for example, those suitable for oral administration may include flavoring agents.

The 1,2-dithiin compounds described herein intended to be used as antifungal agentscan be administered intravenously in a range of about 0.1 to about 400 mg/kg body weight, preferably about 0.1 to about 25 mg/kg body weight.

The 1,2-dithiin compounds described herein intended to be used as antifungal agents can be administered intraperitoneally in a range of about 0.1 to about 400 mg/kg body weight, preferably about 0.1 to about 25 mg/kg body weight.

The 1,2-dithiin compounds described herein intended to be used as antifungal agents can be administered subcutaneously in a range of about 1 to about 400 mg/kg body weight, preferably about 1.0 to about 40 mg/kg body weight.

The 1,2-dithiin compounds described herein intended to be used as antifungal agents can be administered intramuscularly in a range of about 1 to about 400 mg/kg body weight, preferably about 1.0 to about 40 mg/kg body weight.

The 1,2-dithiin compounds described herein intended to be used as antifungal agents can be administered orally in a range of about 1 to about 400 mg/kg body weight, preferably about 1.0 to about 50 mg/kg body weight.

The 1,2-dithiin compounds described herein intended to be used as antifungal agents can be administered topically including to skin, ocular, and oral tissues in a range of about 1.0 to about 15% by weight of the formulation, preferably about 5.0 to about 15% by weight of the formulation.

The 1,2-dithiin compounds described herein intended to be used as antifungal agents can be administered by aerosol in a range of about 1.0 to about 400 mg/kg body weight, preferably about 5.0 to about 50 mg/kg body weight/day.

The novel 1,2-dithiin compounds described herein are also useful as an active agent in an antiseptic, disinfectant or cleaning composition which has fungicidal and/or fungistatic, and/or anti-bacterial and/or anti-viral properties. In one illustrative example, the antiseptic, disinfectant or cleaning composition can be used to disinfect or clean laboratory glassware such as petri dishes, agar plates, etc. or containers use to contain media for growing or maintaining fungal, bacterial or viral cultures. Such antiseptic, disinfectant or cleaning compositions embraced by the present invention can be used to clean glassware or containers as described above which have been used at least once for growing or maintaining fungal, bacterial or viral cultures. Alternatively, the antiseptic, disinfectant or cleaning composition can be used to disinfect or clean glassware or containers which have not yet been used. In another illustrative example, the antiseptic, disinfectant or cleaning composition can be used to disinfect and/or clean surfaces or areas of a home, such as sinks, tubs, bathroom floors, etc. which have been used by a person infected with a fungal, bacterial or viral infection.

The following series of Examples are presented by way of illustration and not by way of limitation on the scope of the invention.

EXAMPLE: SYNTHESIS OF 1,2-DITHIIN COMPOUNDS

MATERIALS AND METHODS

Tetrahydrofuran (THF) was distilled from potassium/ benzophenone; benzene, triethylamine and methylene chloride were distilled from calcium hydride. Anhydrous dimethylformamide (DMF) was obtained from Aldrich. All reactions involving dithiins were done under red light (darkroom!) conditions only. All moisture-sensitive reactions were done under a nitrogen atmosphere, using dry solvents, and all reactions were monitored by TLC. Reaction mixtures following workup were dried over $Na_2SO_4$ or $MgSO_4$ and then filtered before rotary evaporation. Evaporation of solvents was done at room temperature unless otherwise noted. All other reagents were used as received. Flash column chromatography was performed on E. Merck 60 silica gel (230–400 mesh) using nitrogen pressure. TLC was performed on E. Merck Kieselgel 60 $F_{254}$ aluminum plates, and the developed plates were visualized by UV or visible light. $^1H$ and $^{13}C$ NMR were recorded on a Varian Unity Plus 400 MHz or a Varian Unity 400 MHz spectrometer with chloroform as an internal reference unless otherwise noted. NMR shifts were expressed in ppm downfield from internal tetramethylsilane, and NMR coupling constants are reported in Hertz. NMR assignments were determined on the basis of COSY, NOESY, HMQC, HMBC and DEPT experiments performed on selected intermediates. Low resolution mass spectra were recorded on a Kratos MS50 or a Kratos Profile spectrometer. High resolution mass spectra were recorded at Shaman Pharmaceuticals on a Kratos MS50 spectrometer, or were performed by the Analytical Services Department at the University of California, Berkeley. Elemental analyses were performed by the Analytical Services Department at the University of California, Berkeley. Analytical samples of most 1,2-dithiins were purified by reverse-phase HPLC. Preparative HPLC was performed using a Rainin HPLC equipped with two SD-1 pumps and UV-1 detector, with detection at 254 nm, and using a Hamilton PRP-1 reverse-phase column with an acetonitrile-water solvent gradient. Analytical HPLC was performed on a Rainin HPLC equipped with two SD-1 pumps, a PDA-1 diode array detector, and a Sedex 55 light scattering detector, using a Hamilton PRP-1 reverse-phase column with an acetonitrilewater solvent gradient. Melting points were determined using a Buchi model 535 melting point apparatus and are uncorrected.

1,2-DITHIIN COMPOUNDS SYNTHESIZED

EXAMPLE 1

3-(Hydroxymethyl)-6-[(phenyloxy)methyl]-1,2-dithiin.

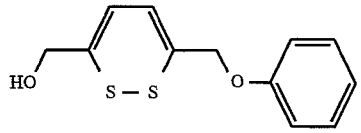

To a stirred solution 3-(hydroxymethyl)-6-[(tert-butyldimethylsilyloxy)methyl]-1,2-dithiin (U.S. Ser. No. 08/212,096) (200 mg, 0.688 mmol), phenol (150 mg, 1.59 mmol), triphenylphosphine (220 mg, 0.839 mmol) in 2 mL of dry THF, cooled in an ice bath, was added diethylazodicarboxylate (DEAD) (144 mg, 0.827 mmol) in one portion. The reaction mixture was stirred for 3.5 h in an ice-water bath after which time TLC showed disappearance of the starting alcohol. The reaction mixture was applied directly to a column of silica gel and eluted with ethyl acetate-hexanes, 1:7, to yield 250 mg of an orange oil. The crude ether was dissolved in acetonitrile (3 mL) and cooled with an ice-water bath. This solution was then treated with 4 mL of a recently prepared solution of $HF/CH_3CN$ (4 mL, prepared by adding 1 mL of aqueous HF to 3 mL of acetonitrile). The resulting orange solution was stirred for 45 min in an ice bath, and then a solution of 10% aqueous potassium carbonate was added cautiously until evolution of $CO_2$ ceased (approx 25 mL). This solution was diluted with 25 mL of saturated aqueous NaCl and extracted with ethyl acetate (2×50 mL). The combined ethyl acetate phases were washed with saturated aqueous NaCl (2×50 mL), dried ($Na_2SO_4$), and concentrated in vacuo to yield 95 mg of an orange oil. Purification by flash chromatography (ethyl acetate-hexane, 1:2) yielded 44.2 mg of the title compound as an orange oil; $^1H$ NMR ($CDCl_3$):δ7.26 (dd, 3 H, J=7.60, J=7.60), 6.93 (dd, 2 H, J=7.60, J=0.80), 6.47 (d, 1 H, J=6.40), 6.38 (d, 1 H, J=6.40), 4.87 (s, 1 H, OH), 4.68 (s, 2 H), 4.18 (s, 2 H); $^{13}C$ NMR ($CDCl_3$):δ159.61, 137.75, 131.16, 130.53, 128.41, 125.53, 122.48, 116.17, 70.87, 64.78; MS (LSIMS) 252 (M+). HRMS (EI) calcd for $C_{12}H_{12}O_2S_2$:252.0278, found:252.0277

EXAMPLE 2

3-[(tert-Butyldimethylsilyloxy)methyl]-6-[(pyridyl-2-oxy)methyl]-1,2-dithiin (A) and 3-[(tert-Butyldimethyl-silyloxy)methyl]-6-[(pyrid-2-one-1-yl)methyl]-1,2-dithiin (B).

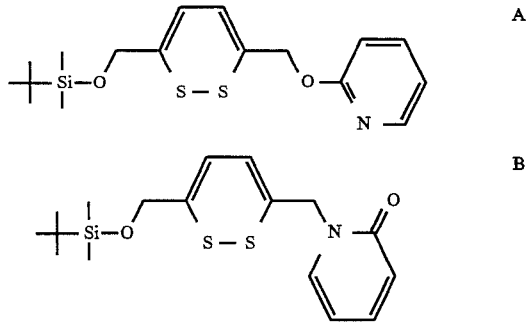

To a stirred solution of 200 mg (0.688 mmol) of 3-(hydroxymethyl)-6-[(tert-butyldimethylsilyloxy)methyl]-1,2-dithiin (U.S. Ser. No. 08/212,096) in 2 mL dry THF was added a solution of 2-hydroxypyridine (132 mg, 1.376 mmol) in 2 mL THF, followed by the addition 220 mg (0.839 mmol) of triphenylphosphine. The resulting solution was cooled to 0° C., then 140 μL (155 mg, 0.890 mmol) of diethylazodicarboxylate was added, and the reaction mixture was kept at 0°–5° C. for 2 h until TLC analysis showed the reaction to be complete. The reaction mixture was loaded directly onto a column of silica gel and chromatographed using ethyl acetate-hexane, 1:6, providing the title pyridyl ether (45 mg, 17.8%). Further elution with ethyl acetate-hexane, 1:3, provided the title pyridone (137 mg, 72.2%). Title pyridyl ether: $^1H$-NMR ($CDCl_3$) δ8.14 (d, J=3.6, 1 H), 7.58 (t, J=7.2, 1 H), 6.89 (t, J=6.0, 1 H), 6.79 (d, J=8.4, 1 H), 6.48 (d, J=5.6, 1 H), 6.36 (d, J=6.4, 1 H), 4.98 (s, 2 H), 4.29 (s, 2 H), 0.91 (s, 9 H), 0.10 (s, 6 H); $^{13}C$—NMR ($CDCl_3$; one quarternary carbon missing) δ146.63, 138.73, 135.97, 130.18, 127.51, 123.54, 117.22, 111.17, 67.01, 64.82, 25.76, 18.30, −5.42; MS (+LSIMS) 367.2 (M+).

Title pyridone: ¹H-NMR (CDCl₃) δ7.39 (d, J=6.81, 1 H), 7.34 (t, J=7.6, 1 H), 6.59 (d, J=8.8, 1 H), 6.34 (s, 2 H), 6.21 (t, J=6.42 1 H), 4.72 (s, 2 H), 4.27 (s, 2 H), 0.90 (s, 9 H), 0.09 (s, 6 H); ¹³C—NMR (CDCl₃) δ164.15, 139.68, 136.74, 136.37, 128.85, 128.53, 123.63, 121.13, 106.24, 64.75, 51.89, 25.74, 18.28, −5.44; MS (+LSIMS) 367.2 (M+).

EXAMPLE 3

3-(Hydroxymethyl)-6-[(pyridyl-2-oxy)methyl]-1,2-dithiin.

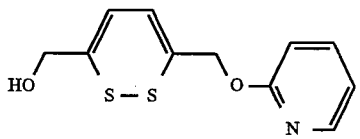

To a stirred solution of the 3-[(tert-butyldimethylsilyloxy)methyl]-6-[(pyridyl-2-oxy)methyl]-1,2-dithiin obtained from Example 2 (40 mg, 0.1 mmol) in 1 mL THF was added a mixture of 1.2 mL of 1M tetrabutylammonium fluoride in THF and 0.7 mL of acetic acid. The reation mixture was stirred for 2.5 h until TLC analysis showed the reaction to be complete. The reaction mixture was concentrated in vacuo and the residue was partitioned between 20 mL of water and 30 mL ethyl acetate. The separated organic phase was washed with dilute aqueous sodium bicarbonate, water, dried over sodium sulfate, and then evaporated to a small volume. The residue was purified by flash chromatography (ethyl acetate-hexane, 1:3) to yield 20 mg (72.7%) of the title compound; ¹H-NMR (CD₃OD) δ8.11 (d, J=4.8, 1 H), 7.69 (t, J=6.8, 1 H), 6.96 (t, J=6.2, 1 H), 6.83 (d, J=8.4, 1 H), 6.50 (d, J=6.4, 1 H), 6.39 (d, J=5.6, 1 H), 4.88 (s, 2 H), 4.18 (s, 2 H); ¹³C—NMR (CD₃OD) δ164.36, 147.75, 140.51, 137.91, 131.53, 128.88, 125.57, 118.63, 112.08, 68.15, 64.79; MS (EI) 253.0 (M+); IR (CHCl₃) 1598, 1570 cm⁻¹. HRMS (EI) calcd for C₁₁H₁₁NO₂S₂:253.02312, found:253.02372.

EXAMPLE 4

3-(Hydroxymethyl)-6-[(pyrid-2-one-1-yl)methyl]-1,2-dithiin.

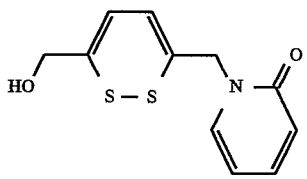

To a stirred solution of the 3-[(tert-butyldimethylsilyloxy)methyl)-6-[(pyrid-2-one-1-yl)methyl]-1,2-dithiin obtained from Example 2 (130 mg, 0.35 mmol) in 2 mL THF was added a mixture of 2.4 mL of 1M tetrabutylammonium fluoride in THF and 1.4 mL of acetic acid. The reation mixture was stirred for 3 h until TLC analysis showed the reaction to be complete; then it was concentrated in vacuo. The residue was partitioned between 30 mL of water and 40 mL ethyl acetate. The organic phase was washed with dilute aqueous sodium bicarbonate, water, dried over sodium sulfate, and then evaporated to a small volume. Purification by flash chromatography (ethyl acetate) yielded 52 mg (58.0%) of the title compound; ¹H-NMR (CD₃OD):δ7.68 (d, J=6.8, 1 H), 7.55 (dt, J=7.2, 7.2, 1.6, 1 H), 6.56 (d, J=8.9, 1 H), 6.43–6.37 (m, 3 H), 4.70 (s, 2 H), 4.17 (s, 2 H); ¹³C—NMR (CD₃OD):δ164.67, 142.49, 139.41, 138.16, 130.49, 129.96, 125.64, 120.87, 108.74, 64.71, 53.04; MS (+LSIMS) 254.0 (MH+); IR υC=O 1654, 1575, 1538 cm⁻¹. HRMS (EI) calcd for C₁₁H₁₁NO₂S₂:253.0231, found:253.0225.

EXAMPLE 5

3-(Hydroxymethyl)-6-[(pyridyl-3-oxy)methyl]-1,2-dithiin.

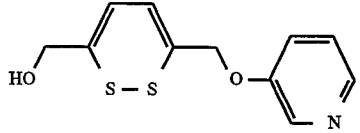

To a stirred solution of 3-(hydroxymethyl)-6-[(tert-butyldimethylsilyloxy)methyl]-1,2-dithiin (U.S. Ser. No. 08/212,096) (200 mg, 0.688 mmol) in 2 mL dry THF was added a solution of 3-hydroxypyridine (132 mg, 1.376 mmol) in 2 mL THF, followed by addition of triphenylphosphine (220 mg, 0.839 mmol). The resulting solution was cooled to 0° C., 140 μL (155 mg, 0.890 mmol) of diethylazodicarboxylate was added, and the reaction mixture was kept at 0°–5° C. with stirring for 2 h until TLC analysis showed the reaction to be complete. The reaction mixture was poured directly onto a silica gel column for purification using ethyl acetate-hexane (1:3), yielding 46 mg (18.3%) of 3-[(tert-butyldimethylsilyloxy)methyl]-6-[(pyridyl-3-oxy)methyl]-1,2-dithiin; ¹H-NMR (CDCl₃):δ8.36 (s, 1 H), 8.26 (d, J=2.0 1 H), 7.23 (d, J=2.4, 2 H), 6.45 (d, J=4.8, 1 H), 6.38 (d, J=4.8, 1 H), 4.72 (s, 2 H), 4.30 (s, 2 H), 0.92 (s, 9 H), 0.10 (s, 6 H); MS (+LSIMS) 367.2 (M+).

To a stirred solution of the 3-[(tert-butyldimethylsilyloxy)methyl]-6-[(pyridyl-3-oxy)methyl]1,2-dithiin obtained above (40 mg, 0.1 mmol) in 1 mL THF was added a mixture of 1.2 mL of 1M tetrabutylammonium fluoride in THF and 0.7 mL of acetic acid. The reation mixture was stirred for 2.5 h until TLC analysis showed the reaction to be complete, then concentrated in vacuo. The residue was partitioned between 20 mL of water and 30 mL of ethyl acetate. The separated organic phase was washed with dilute aqueous sodium bicarbonate, water, dried over sodium sulfate, and then evaporated to a small volume. The residue was chromatographed over a silica gel column (ethyl acetate-hexane, 2:1) to yield 21 mg (76.3%) of the title compound as yellow crystals, mp 97°– 98° C.; ¹³H-NMR (CD₃OD) δ8.28 (d, J=2.4, 1 H), 8.15 (dd, J=6.0, J=1.2, 1 H), 7.49–7.46 (m, 1 H), 7.38 (dd, J=8.4, J=8.8, 1 H), 6.54 (d, J=6.4, 1 H), 6.41 (d, J=6.4, 1 H), 4.82 (s, 2 H), 4.19 (s, 2 H); ¹³C—NMR (CD₃OD) δ168.40, 156.32, 142.96, 139.01, 138.56, 129.43, 125.77, 125.35, 124.08, 71.23, 64.68; MS (+LSIMS) 253.1 (M+). HRMS (EI) calcd for C₁₁H₁₁NO₂S₂:253.0231, found:253.0239. Anal. calcd for C₁₁H₁₁NO₂S₂:C, 52.15; H, 4.37; N, 5.53. Found:C, 52.49; H, 4.48; N, 5.35.

EXAMPLE 6

3-(tert-Butyldimethylsilyloxy)phenol.

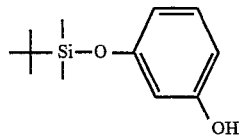

To a solution of resorcinol (5.5 g, 50 mmol) in anhydrous DMF (15 mL) was added imidazole (7.14 g, 210 mol %) and tert-butyldimethylsilyl chloride (7.53 g, 105 mol %). The reaction mixture was stirred for 20 h. The reaction mixture was diluted with water (a white precipitate formed) and then it was extracted with ether (3×300 mL). The combined extract was dried ($Na_2SO_4$), filtered and concentrated to yield 5.4 g (48.3%) of the title compound; $^1$H-NMR ($CDCl_3$) δ7.07 (t, 1 H, J=8.0), 6.42 (pseudot, 2 H, J=7.6), 6.36 (s, 1 H), 5.06 (bs, 1 H), 0.98 (s, 9 H), 0.20 (s, 6 H); $^{13}$C—NMR ($CDCl_3$) δ157.90, 156.51, 129.89, 112.66, 108.42, 107.53, 25.61, 18.14, 14.49.

EXAMPLE 7

3-(Hydroxymethyl)-6-[(3-hydroxyphenyloxy)methyl]-1,2-dithiin.

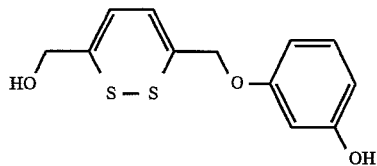

To a stirred solution of 3-(hydroxymethyl)-6-[(tert-butyldimethylsilyloxy)methyl]-1,2-dithiin (U.S. Ser. No. 08/212,096) (200 mg, 0.688 mmol) in 2 mL dry THF was added a solution of 3-(tert-butyldimethylsilyloxy)phenol (164 mg, 0.732 mmol) in 2 mL THF, followed by addition of triphenylphosphine (220 mg, 0.839 mmol). The resulting solution was cooled to 0° C., 140 μL (155 mg, 0.890 mmol) of diethylazodicarboxylate was added, and then the reaction mixture was kept at 0°–5° C. for 3 h until TLC analysis showed the reaction to be complete. For isolation of the products, the reaction mixture was chromatographed directly on a silica gel column, using ethyl acetate-hexane, 1:6, to give 3-[(tert-butydimethylsilyloxy)methyl)-6-[[(3-tert-butyldimethylsilyloxy)phenyloxy]methyl]-1,2-dithiin (242 mg, 70.9%) as an orange oil; $^1$H-NMR ($CDCl_3$) δ7.07 (t, J=8.0, 1 H), 6.50 (dd, J=8.0, J=2.4, 1 H), 6.47–6.38 (m, 3 H), 6.32 (d, J=6.4, 1 H), 4.59 (s, 2 H), 4.25 (s, 2 H), 0.94 (s, 9 H), 0.87 (s, 9 H), 0.16 (s, 6 H), 0.06 (s, 6 H); $^{13}$C—NMR ($CDCl_3$) δ159.19, 156.82, 135.88, 129.74, 129.35, 126.78, 123.54, 113.42, 107.94, 107.46, 69.68, 64.84, 25.80, 25.68, 18.35, 18.20 –4.40, –5.37; MS (+LSIMS) 496.3 (M+).

To a stirred solution of the 3-[(tert-butydimethyl-silyloxy)methyl)-6-1[[(3-tert-butyldimethylsilyloxy)phenyloxy]methyl]-1,2-dithiin obtained above (210 mg, 0.42 mmol) in 2 mL THF was added a mixture of 5 mL of 1M tetrabutylammonium fluoride in THF and 4 mL of acetic acid. The reation mixture was stirred for 3 h until TLC analysis showed the reaction to be complete, then concentrated in vacuo. The residue was partitioned between 40 mL of water and 60 mL ethyl acetate. The organic phase was washed with dilute aqueous sodium bicarbonate, water, dried over sodium sulfate, and then evaporated to a small volume. The residue was purified by flash chromatography, yielding 95 mg (84.8%) of the title compound as yellow crystals, mp 116° C.; $^1$H-NMR ($CD_3OD$) δ7.06 (t, J=8.0, 1 H), 6.48–6.38 (m, 5 H), 4.64 (s, 2 H), 4.18 (s, 2 H); $^{13}$C—NMR ($CD_3OD$) δ160.82, 159.69, 137.65, 131.22, 130.94, 128.26, 125.52, 109.64, 107.14, 103.51, 70.78, 64.75; MS (+LSIMS) 268.0 (M+). HRMS (EI) calcd for $C_{12}H_{12}O_3S_2$:268.0228, found:268.0243. Anal. calcd for $C_{12}H_{12}O_3S_2$:C, 53.71; H, 4.51. Found:C, 53.50; H, 4.45.

EXAMPLE 8

3-(Hydroxymethyl)-6-[[3-(N,N-dimethylamino)phenyloxy]methyl]-1,2-dithiin.

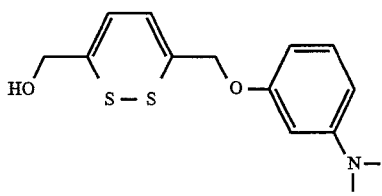

To a stirred solution of 200 mg (0.688 mmol) of 3-(hydroxymethyl)-6-[(tert-butyldimethylsilyloxy)methyl]-1,2-dithiin (U.S. Ser. No. 08/212,096) in 2 mL dry THF was added a solution of 3—N,N-dimethylaminophenol (190 mg, 1.376 mmol) in 2 mL THF, followed by addition of (220 mg, 0.839 mmol) triphenylphosphine. The resulting solution was cooled to 0° C., then 140 μL (155 mg, 0.890 mmol) of diethylazodicarboxylate was added, and the reaction mixture was kept at 0°–5° C. for 3 h until TLC analysis showed the reaction to be complete. For isolation of the products the reaction mixture was chromatographed directly on silica gel column, using ethyl acetate-hexane, 1:3 to yield 3-[tert-butyldimethylsilyloxy)methyl]-6-[[3-(N,N-dimethylamino)-phenyloxy]methyl]-1,2-dithiin (115 mg, 41.1%); $^1$H-NMR ($CDCl_3$) δ7.3 (bs, 1 H), 7.1 (bs, 1 H), 6.60 (d, J=2.4, 1 H), 6.52 (bd, J=7.27 1 H), 6.42 (d, J=6.0, 1 H), 6.34 (d, J=6.0, 1 H), 4.60 (s, 2 H), 4.26 (s, 2 H), 2.65 (s, 6 H), 0.88 (s, 9 H), 0.07 (s, 6 H).

To a stirred solution of the 3-[(tert-butyldimethylsilyloxy)methyl]-6-[[3-(N,N-dimethylamino)-phenyloxy]methyl]-1,2-dithiin obtained above (100 mg, 0.24 mmol) in 2 mL THF was added a mixture of 2.4 mL of 1M tetrabutylammonium fluoride in THF and 1.4 mL of acetic acid. The reation mixture was stirred for 3 h until TLC analysis showed the reaction to be complete, then concentrated in vacuo. The residue was partitioned between 40 mL of water and 60 mL ethyl acetate. The organic phase was washed with dilute aqueous sodium bicarbonate, water, dried over sodium sulfate, and then evaporated to a small volume. The residue was chromatographed over silica gel column (ethyl acetate-hexane, 1:1) to yield 60.5 mg (84.0%) of the title compound. Further purification was accomplished by reverse-phase HPLC (PRP-1 column, acetonitrile-water, 2:3); $^1$H-NMR ($CDCl_3$) δ7.3 (bs, 1 H), 7.1 (bs, 1 H), 6.64 (s, 1 H), 6.55 (d, J=7.2, 1 H), 6.46(d, J=5.6, 1 H), 6.41 (d, J=5.6, 1 H), 4.65 (s, 2 H), 4.30 (s, 2 H), 2.69 (s, 6 H).

EXAMPLE 9

3-(tert-Butyldimethylsilyloxy)pyridazine-6-ol.

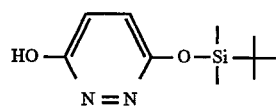

To a suspension of 3,6-dihydroxypyrazidine (5 g, 44 mmol) in anhyd DMF (100 mi) was added imidazole (6.28 g, 105 mol %) and tert-butyldimethylsilyl chloride (7.06 g, 210 mol %), and the clear solution which formed was stirred for 3 h at rt. The reaction mixture was diluted with water (a white precipitate formed) and then it was extracted with ether (3×300 mL). The combined extract was dried (Na$_2$SO$_4$), filtered and concentrated to yield 8.4 g (84.1%) of the title compound; $^1$H—NMR (CDCl$_3$) δ6.93 (d, 2 H, J=2.80), 0.94 (s, 9 H), 0.27 (s,6 H); $^{13}$C—NMR (CDCl$_3$) δ161.31, 152.54, 132.59, 130.19, 25.54, 17.80, −4.80.

EXAMPLE 10

3-[(tert-Butyldimethylsilyloxy)methyl]-6-[(3-hydroxypyridazin-6-one-1-yl)methyl]-1,2-dithiin (C) and [(tert-Butyldimethylsilyloxy)methyl]-6-[(3-hydroxypyridazine-6-oxy)methyl]-1,2-dithiin (D).

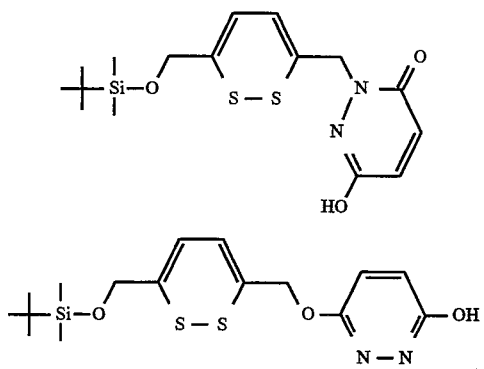

To a stirred solution of 3-(hydroxymethyl)-6-[(tert-butyldimethylsilyloxy)methyl]-1,2-dithiin (U.S. Ser. No. 08/212,096) (200 mg, 0.688 mmol) in 2 mL dry THF was added a solution of the resulting compound of Example 9 (164 mg, 0.732 mmol) in 2 mL THF, followed by the addition of triphenylphosphine (220 mg, 0.839 mmol). The resulting solution was cooled to 0° C., then 140 µL (155 mg, 0.890 mmol) of diethylazodicarboxylate was added, and the reaction mixture was kept at 0°–5° C. for 3 h until TLC analysis showed the reaction to be complete. For isolation of the products the reaction mixture poured directly onto a column of silica gel and chromatographed using ethyl acetate-hexane, 1:6 to yield two products. The first isolated was 3-[(tert-butyldimethylsilyloxy)methyl]-6-[(3-hydroxypyrazidin-6-one-1-yl)methyl]-1,2-dithiin (85 mg, 25.1%). The slightly more polar product was [(tert-butyldimethylsilyloxy)methyl]-6-[(3-hydroxypyrazidine-6-oxy)methyl]-1,2-dithiin (37 mg, 10.9%). Both products were used without further purification.

EXAMPLE 11

3-(Hydroxymethyl)-6-[(3-hydroxypyridazin-6-one-1-yl)methyl]-1,2-dithiin.

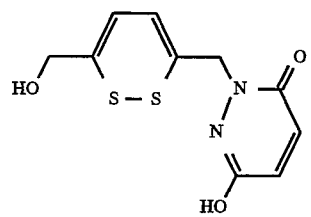

To a stirred solution of the [(tert-butyldimethylsilyloxy)methyl]-6-[(3-hydroxypyrazidin-6-one-1-yl)methyl]-1,2-dithiin obtained in Example 10 (30 mg, 0.42 mmol) in I mL THF was added a mixture of 1.2 mL of 1M tetrabutylammonium fluoride in THF and 0.8 mL of acetic acid. The reation mixture was stirred for 3 h until TLC analysis showed the reaction to be complete, then concentrated in vacuo. The residue was partitioned between 20 mL of water and 30 mL ethyl acetate. The organic phase was washed with dilute aqueous sodium bicarbonate, water, dried over sodium sulfate, and then evaporated to a small volume. The residue was purified by silica gel chromatography (ethyl acetate-hexane, 1:1) to yield 8 mg (49.5%) of the title compound; $^1$H-NMR (CD$_3$OD) δ7.15 (d, J=9.60, 1 H), 6.97 (d, J=10.0, 1 H), 6.38 (s, 2 H), 4.78 (s, 2 H), 4.19 (s, 2 H); $^{13}$C—NMR (CD$_3$OD) δ160.88, 155.29, 137.60, 133.54, 130.44, 129.45, 129.06, 125.66, 64.73, 55,35; MS (+LSIMS) 271.1 (M+).

EXAMPLE 12

3-(Hydroxymethyl)-6-[(3-hydroxypyridazine-6-oxy)methyl]-1,2-dithiin.

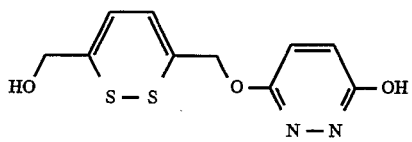

To a stirred solution of the 3-[(tert-butyldimethylsilyloxy)methyl]-6-[(3-hydroxypyrazidine-6-oxy)methyl]-1,2-dithiin obtained in Example 10 (85 mg, 0.42 mmol) in 1 mL THF was added a mixture of 2.4 mL of 1M tetrabutylammonium fluoride in THF and 1.2 mL of acetic acid. The reation mixture was stirred for 3 h until TLC analysis showed the reaction to be complete, then concentrated in vacuo. The residue was partitioned between 40 mL of water and 60 mL ethyl acetate. The organic phase was washed with dilute aqueous sodium bicarbonate, water, dried over sodium sulfate, and then concentrated to a small volume. The residue was purified by silica gel chromatography (ethyl acetate-hexane, 1:1) to yield 21 mg (45.6%) of the title compound; $^1$H-NMR (CD$_3$OD) δ7.23 (d, J=10.0, 1 H), 7.03 (d, J=9.6, 1 H), 6.55 (d, 2 H, J=6.0), 6.41 (d, 2 H, J=6.0); 4.84 (s, 2 H), 4.20 (s, 2 H); $^{13}$C—NMR (CD$_3$OD) δ160.88, 153.94, 137.44, 138.44, 130.38, 130.15, 128.91, 125.62, 69.39, 64.70; MS (+LSIMS) 271.0 (M+).

EXAMPLE 13

3-(Hydroxymethyl)-6-[(2-trifluoromethylphenyloxy)methyl]-1,2-dithiin.

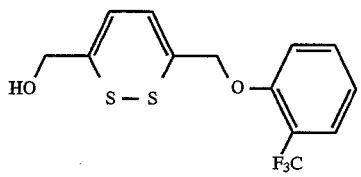

To a stirred solution of 3-(hydroxymethyl)-6-[(tert-butyldimethylsilyloxy)methyl]-1,2-dithiin (U.S. Ser. No. 08/212,096) (200 mg, 0.69 mmol) in 5 mL dry THF was added a solution of 2-(trifluoromethyl)phenol (223 mg, 1.37 mmol) in 5 mL THF, followed by addition of triphenylphosphine (234 mg, 0.89 mmol) The resulting solution was cooled to 0° C., then 140 µL (156 mg, 0.89 mmol) of diethylazodicarboxylate was added, and the reaction mixture was kept at 0°–5° C. until TLC analysis showed the reaction to be complete. For isolation of the products, the reaction mixture poured directly onto a silica gel column using ethyl acetate-hexane, 1:3, to provide 110 mg (37%) of 3-[(tert-butyldimethylsilyloxy)methyl]-6-[(2-trifluoromethylphenyloxy)methyl]-1,2-dithiin; $^1$H NMR (CDCl$_3$):δ7.56 (d, J=8.0, 1 H), 7.45 (t, J=8.0, 1 H), 7.01 (m, 2 H), 6.49 S (d, J=6.0 Hz, 1 H), 6.37 (d, J=6.0 Hz, 1 H), 4.71 (s, 2 H), 4.26 (s, 2 H), 0.88 (s, 9 H), 0.07 (s, 6 H); $^{13}$C NMR (CDCl$_3$):δquaternary carbons missing, 136.19, 133.24, 127.23, 123.57, 120.81, 113.15, 69.58, 64.85, 25.79, 18.34, –5.38; MS (LSIMS) (M+) 434.1.

To a stirred solution of the 3-[(tert-butyldimethylsilyloxy)methyl]-6-[(2-trifluoromethylphenyloxy)methyl]-1,2-dithiin obtained above (70 mg, 0.16 mmol) in 2 mL THF was added a mixture of 1.0 mL of 1M tetrabutylammonium fluoride in THF and 0.6 mL of acetic acid. The reation mixture was stirred for 7 h until TLC analysis showed the reaction to be complete, then concentrated in vacuo. The residue was partitioned between 20 mL of water and 20 mL ethyl acetate. The organic phase was washed with 3% solution of aqueous sodium bicarbonate (50 mL), water, dried over sodium sulfate, and then concentrated to a small volume. The residue was purified by silica gel chromatography (ethyl acetate-hexane, 1:3) to yield 30 mg (58%) of the title compound; $^1$H NMR (CDCl$_3$):δ7.60 (dd, J=8.0, J=1.6, 1 H), 7.50 (t, J=8.4, 1 H), 7.08 (t, J=8.0, 1 H), 6.99 (d, J=8.0 Hz, 1 H), 6.54 (d, J=6.0 Hz, 1 H), 6.44 (d, 1 H, J=6.0), 4.76 (s, 2 H), 4.30 (s, 2 H), 1.93 (bs, 1 H); $^{13}$C NMR (CDCl$_3$):161.14, 135.73, 133.26, 128.84, 127.31 (q, J=5.4), 126.59, 125.06, 123.33, 120.90, 113.11, 69.45, 64.59; EI-MS:m/z 320.62.

EXAMPLE 14

3-(Hydroxymethyl)-6-[(2-fluorophenyloxy)methyl]-1,2-dithiin.

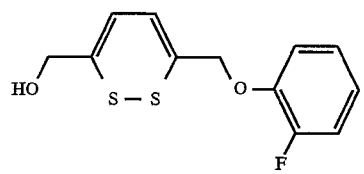

To a stirred solution of 3-(hydroxymethyl)-6-[(tert-butyldimethylsilyloxy)methyl]-1,2-dithiin (U.S. Ser. No. 08/212,096) (350 mg, 1.20 mmol) in 5 mL dry THF was added a solution of 2-fluorophenol (270 mg, 215 µL, 2.40 mmol) in 5 mL THF, followed by addition of triphenylphosphine (385 mg, 2.40 mmol). The resulting solution was cooled to 0° C., then 245 µL (271 mg, 2.40 mmol) of diethylazodicarboxylate was added, and the reaction mixture was kept at 0°–5° C. for 30 min, and then the ice bath was removed. The reaction was stirred for 2 d at rt; some starting material still remained by TLC analysis. For isolation of the products, the reaction mixture poured directly onto a silica gel column using ethyl acetate-hexane, 1:3, to provide 329 mg (71%) of 3-[(tert-butyldimethylsilyloxy)methyl]-6-[(2fluoromethylphenyl-oxy)methyl]-1,2-dithiin; $^1$H NMR (CDCl$_3$) δ7.7–6.83 (m, 4 H), 6.47 (d, J=6.0, 1 H), 6.38 (d, J=6.0, 1 H), 4.8 ( s, 2 H), 4.26 (s, 2 H), 0.92 (s, 9 H), 0.10 (s, 6 H).

To a stirred solution of the 3-[(tert-butyldimethylsilyloxy)methyl]-6-[(2fluoromethylphenyloxy)methyl]-1,2-dithiin obtained above (250 mg, 0.65 mmol) in 5 mL THF was added a mixture of 3.0 mL of 1M tetrabutylammonium fluoride in THF and 2.0 mL of acetic acid. The reation mixture was stirred for 5 h until TLC analysis showed the reaction to be complete, then concentrated in vacuo. The residue was partitioned between 20 mL of water and 20 mL ethyl acetate. The organic phase was washed with 3% solution of aqueous sodium bicarbonate (50 mL), water, dried over sodium sulfate, and then concentrated to a small volume. The residue was purified by silica gel chromatography (ethyl acetate-hexane, 1:3) to yield 120 mg (68%) of the title compound; $^1$H NMR (CDCl$_3$):δ7.12–6.9 (m, 4 H), 6.47 (d, J=6.0, 1 H), 6.39 (d, J=6.0, 1 H), 4.74 (s, 2 H), 4.28 (s, 2 H); MS (EI) 270.1 (M$^+$).

EXAMPLE 15

3-[(tert-Butyldimethylsilyloxy)methyl]-6-[(5-nitropyrldyl-2-oxy)methyl]-1,2-dithiin (E) and 3-[(tert-Butyldimethylsilyloxy)methyl]-6-[(5-nitropyrid-2-one-1-ul)methyl]-1,2-dithiin (F).

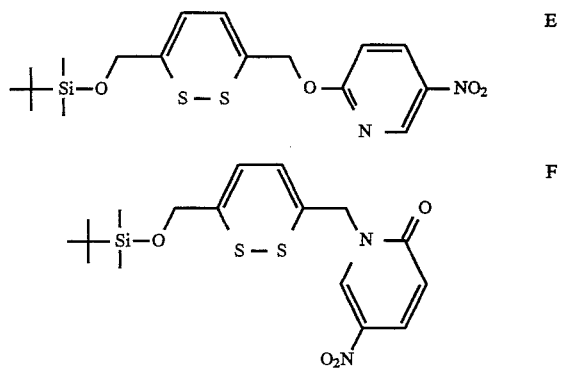

To a stirred solution of 3-(hydroxymethyl)-6-[(tert-butyldimethylsilyloxy)methyl]-1,2-dithiin (650 mg, 2.237 mmol) in 5 mL dry THF was added a solution of 2-hydroxypyridine (470 mg, 3.357 mmol) in 6 mL THF, followed by the addition of triphenylphosphine (715 mg, 2.729 mmol). The resulting solution was cooled to 0° C., then 455 µL (504 mg, 2.892 mmol) of diethylazodicarboxylate was added, and the reaction mixture was kept at 0°–5° C. for 2 h until TLC analysis showed the reaction to be complete. For isolation of the products the reaction mixture poured directly onto a silica gel column using ethyl acetate-hexane, 1:20 for elution, providing 120 mg (13.0%) of the title pyridine. Further elution with ethyl acetate-hexane, 1:6, provided the title pyridone, (373 mg, 40.5%).

Title pyridine: $^1$H-NMR (CDCl$_3$) δ9.07 (d, J=2.8, 1 H), 8.37 (d, J=2.4, 1 H), 7.52–7.43 (m, 1 H), 6.49 (d, J=6.4, 1 H), 6.38 (d, J=5.6, 1 H), 5.09 (s,2 H), 4.23 (s,2 H), 0.92 (s,9 H), 0.10 (s,6 H). $^{13}$C—NMR (CDCl$_3$) δ160.22, 144.52 137.10, 134.18, 132.18, 131.48, 123.33, 111.44, 68.48, 64.72, 60.80, 25.74, 18.30, −5.31.

Title pyridone: $^1$H-NMR (CDCl$_3$) δ8.82 (d, J=2.8, 1 H), 8.12 (dd, J=2.8, J=10.4, 1 H), 6.60 (d, J=10.4, 1 H), 6.53 (d, J=6.0, 1 H), 6.41 (d, J=6.0, 1 H), 4.76 (s,2 H), 4.30 (s,2 H), 0.91 (s, 9 H), 0.10 (s, 6 H). $^{13}$C—NMR (CDCl$_3$) δ quaternary carbons missing, 138.45, 133.35 131.45, 125.65, 123.38, 119.63, 64.61, 53.00, 25.73, 18.28, −5.45.

EXAMPLE 16

3-(Hydroxymethyl)-6-[(5-nitropyrldyl-2-oxy)methyl]-1,2-dithiin.

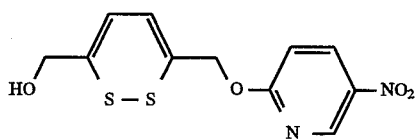

To a stirred solution of the 3-[tert-butyldimethysilyloxy)methyl]-6-[(5-nitropyridyl-2-oxy)methyl]-1,2-dithiin obtained in Example 15 (165 mg, 0.55 mmol) in 6 mL THF was added a mixture of 7.2 mL of 1M tetrabutylammonium fluoride in THF and 4.5 mL of acetic acid. The reaction mixture was stirred for 2 h at rt until TLC analysis showed the reaction to be complete, then concentrated in vacuo. The residue was partitioned between 40 mL of water and 60 mL of ethyl acetate. The organic phase was washed with dilute aqueous sodium bicarbonate, water, dried over sodium sulfate, and then concentrated to a small volume. The residue was purified by chromatography over a silica gel column (ethyl acetate-hexane, 1:1) to yield 82 mg (69.0%) of the title compound as yellow crystals, m.p. 102°–103° C. Further purification was accomplished by reverse-phase HPLC (PRP column, acetonitrile-water 2:3); $^1$H-NMR (CD$_3$OD) δ9.06 (d, J=3.2, 1 H), 8.48 (dd, J=2.8, J=9.2, 1 H), 7.00 (dd, J=9.2, J=0.40, 1 H), 6.56 (d, J=6.0, 1 H), 6.41 (d, J=6.0, 1 H), 5.13 (s, 2 H), 4.19 (s,2 H); $^{13}$C—NMR (CD$_3$OD) δ167.67, 145.34, 138.69, 135.62, 130.17, 129.92, 125.83, 125.49, 112.53, 69.33, 64.70; MS (EI) 298.0 (MH+). HRMS (EI) calcd for C$_{11}$H$_{10}$N$_2$O$_4$S$_2$:298.00820, found:298.008479. Anal. calcd for C$_{11}$H$_{10}$N$_2$O$_4$S$_2$:C, 44.28; H, 3.38; N, 9.39. Found:C, 43.90; H, 3.47; N, 9.06.

EXAMPLE 17

3-(Hydroxymethyl)-6-[(5-nitropyrid-2-one-1-yl)methyl]-1,2-dithiin.

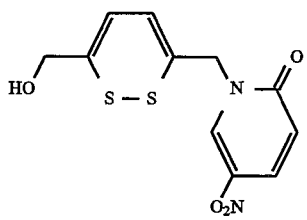

To a stirred solution of the 3-[tert-butyldimethylsilyloxy)methyl]-6-[(5-nitropyrid-2-one-1-yl)methyl]-1,2-dithiin obtained from Example 15 (100 mg, 0.24 mmol) in 2 mL THF was added a mixture of 2.4 mL of 1M tetrabutylammonium fluoride in THF and 1.4 mL of acetic acid. The reaction mixture was stirred 3 h until TLC analysis showed the reaction to be complete, and then it was concentrated in vacuo. The residue was partitioned between 30 mL of water and 40 mL ethyl acetate. The organic phase was washed with dilute aqueous sodium bicarbonate, water, dried over sodium sulfate, and then concentrated to a small volume. The residue was purified by flash chromatography using ethyl acetate to yield 48 mg (66.4%) of the title compound; $^1$H-NMR (CD$_3$OD) δ9.08 (d, 1 H J=3.2), 8.23 (dd, 1 H, J=6.0), 6.59 (d, J=10.0, 1 H), 6.55 (d, J=6.0, 1 H), 6.42 (d, J=6.0, 1 H), 4.86 (overlap with HDO, s, 2 H), 4.19 (s, 2 H); $^{13}$C—NMR (CD$_3$OD) δ163.48, 141.07, 139.11, 135.28, 132.73, 131.59, 128.77, 125.57, 119.87, 64.64, 53.75; MS (EI) 298.0 (M+); IR υC=O 1666.6, 1608, 1562 cm$^{-1}$. HRMS (EI) calcd for C$_{11}$H$_{10}$N$_2$O$_4$S$_2$:298.0082, found:298.0055. Anal. calcd for C$_{11}$H$_{10}$N$_2$O$_4$S$_2$:C, 44.28; H, 3.38; N, 9.39. Found:C, 44.01; H, 3.35; N, 9.15.

EXAMPLE 18

3-(Hydroxymethyl)-6-[(3-ethynylphenyloxy)methyl]-1,2-dithiin.

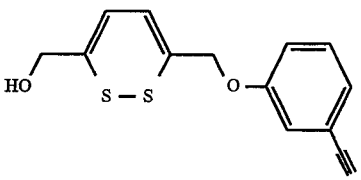

To a stirred solution of 3-(hydroxymethyl)-6-[(tert-butyldimethylsilyloxy)methyl]-1,2-dithiin (U.S. Ser. No. 08/212,096) (235 mg, 0.802 mmol) in 1 mL of dry THF was added a solution of 3-hydroxyphenylacetylene (142 mg, 1.20 mmol) in 1 mL THF, followed by the addition of triphenylphosphine (315 mg, 0.977 mmol). The resulting solution was cooled to 0° C., then 190 μL (210 mg, 1.037 mmol) of diethylazodicarboxylate was added, and the reaction mixture was kept at 0°–5° C. for 1.5 h until TLC analysis showed the reaction to be complete. For 5 isolation of the products, the reaction mixture was chromatographed directly on a silica gel column, using ethyl acetate-hexane, 1:20, to yield 3-[tert-butyldimethylsilyloxy)methyl]-6-[(3-ethynylphenyloxy)methyl]-1,2-dithiin (175 mg, 56.0%); $^1$H-NMR (CDCl$_3$) δ7.23 (t, J=8.0, 1 H), 7.12 (d, J=8.0, 1 H), 7.05 (s, 1 H), 6.93 (dd, J=6.0, 2.4, 1 H), 6.44 (d, J=6.0, 1 H), 6.37 (d, J=6.0, 1 H), 4.66 (s, 2 H), 4.30 (s, 2 H), 3.07 (bs, 1 H), 0.92 (s, 9 H), 0.10 (s, 6 H); $^{13}$C—NMR (CDCl$_3$) δ157.79, 136.21, 132.54, 129.46, 128.74, 127.03, 125.43, 123.45, 118.29, 116.22, 83.28, 77.21, 69.73, 64.79, 25.76, 18.31, −5.41. MS (EI) 390.1 (M+).

To a stirred solution of the 3-[tert-butyldimethylsilyloxy)methyl]-6-[(3-ethynylphenyloxy)methyl]-1,2-dithiin obtained above (160 mg, 0.41 mmol) in 2 mL THF was added a mixture of 3.5 mL of 1M tetrabutylammonium fluoride in THF and 2 mL of acetic acid. The reaction mixture was stirred for 3 h until TLC analysis showed the reaction to be complete; then it was concentrated in vacuo. The residue was partitioned between 40 mL of water and 60 mL ethyl acetate. The organic phase was washed with dilute aqueous sodium bicarbonate, water, dried over sodium sulfate, and then concentrated to a small volume. The residue was chromato-graphed over silica gel column (ethyl acetate-hexane, 1:3) to yield 35 mg (30.9%) of the title compound as yellow crystals, mp 70.5°–71.5° C.; $^1$H-NMR (CDCl$_3$) δ7.46 (t, J=8.4, J=8.4, 1 H), 7.35 (d, J=7.6, 1 H), 7.27 (s, 1 H), 7.16 (d, J=8.0, 1 H), 6.67 (d, J=6.4, 1 H), 6.62 (d, J=5.6, 1 H), 4.98 (s, 2 H), 4.51 (s, 2 H), 3.29 (s, 1 H) 2.1 (bs, 1 H); $^{13}$C—NMR (CDCl$_3$) δ157.71, 135.73, 129.90, 129.50, 126.88, 125.52, 124.91, 123.20, 118.27, 116.22, 83.25, 77.28, 69.62, 64.53; MS (+EI) 276.0 (M+). HRMS (EI) calcd for C$_{14}$H$_{12}$O$_2$S$_2$:276.02787, found: 276.02754. Anal. calcd for C$_{14}$H$_{12}$O$_2$S$_2$:C, 60.84; H, 4.37. Found:C, 60.65; H, 4.39.

EXAMPLE 19

3-(Hydroxymethyl)-6-[methyloxy[methyl benzoate-3-yl]]-1,2-dithiin.

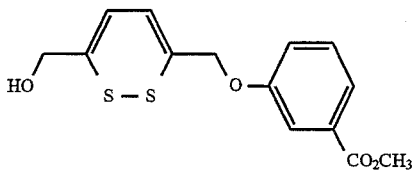

To a stirred solution of 3-(hydroxymethyl)-6-[(tert-butyldimethylsilyloxy)methyl]-1,2-dithiin (U.S. Ser. No. 08/212,096) (235 mg, 0.802 mmol) in 2 mL of dry THF was added a solution of methyl 3-hydroxybenzoate (183 mg, 1.20 mmol) in 1 mL THF, followed by addition of triphenylphosphine (315 mg, 0.977 mmol). The resulting solution was cooled to 0° C., then 190 μL (210 mg, 1.037 mmol) of diethylazodicarboxylate was added, and the reaction mixture was kept at 0°–5° C. for 3 h until TLC analysis showed the reaction to be complete. For isolation Of the products the reaction mixture was chromatographed directly on a silica gel column, using ethyl acetate-hexane, 1:20, to yield 205 mg (60.3%) of 3-[(tert-butyldimethylsilyloxy)methyl]-6-[methyloxy[methyl benzoate-3-yl]]1,2-dithiin; $^1$H-NMR (CDCl$_3$) δ7.67 (d, J=7.6, 1 H), 7.59 (s, 1 H), 7.36 (t, J=8.0, 1 H), 7.14 (d, J=7.6, 1 H), 6.47 (d, J=6.4, 1 H), 6.38 (d, J=6.4, 1 H), 4.72 (s, 2 H), 4.30 (s, 2 H), 3.92 (s,3 H), 0.92 (s, 9 H), 0.11 (s, 6 H); $^{13}$C—NMR (CDCl$_3$) δ166.74, 158.02, 136.34, 131.52, 129.50, 128.64, 127.23, 123.44, 122.76, 120.27, 115.35, 69.88, 64.79, 52.19, 25.77, 18.55, –5.40; MS (EI) 424.1 (M+).

To a stirred solution of the 3-[(tert-butyldimethylsilyloxy)methyl]-6-[methyloxy[methyl benzoate-3-yl]]-1,2-dithiin obtained above (200 mg, 0.47 mmol) in 2 mL of THF was added a solution of 4 mL of 1M tetrabutylammonium fluoride in THF and 2 mL of acetic acid. The reation mixture was stirred for 1 h until TLC analysis showed the reaction to be complete, and then it was concentrated in vacuo. The residue was partitioned between 40 mL of water and 60 mL ethyl acetate. The organic phase was washed with dilute aqueous sodium bicarbonate, water, dried over sodium sulfate, and then concentrated to a small volume. The residue was purified by silica gel chromatography (ethyl acetate-hexane, 1:3), yielding 100 mg (68.5%) of the title compound; $^1$H-NMR (CD$_3$OD) δ7.62 (d, J=7.6, 1 H), 7.56 (s, 1 H), 7.39 (t, J=8.0, 1 H), 7.20 (dd, J=8.0, J=2.0, 1 H), 6.51 (d, J=6.0, 1 H), 6.40 (d, J=6.0, 1 H), 4.76 (s, 2 H), 4.18 (s, 2 H), 3.80 (s, 3 H); $^{13}$C—NMR (CD$_3$OD) δ168.27, 159.65, 138.16, 132.76, 130.81, 130.58, 128.90, 125.49, 123.60, 121.32, 116.75, 71.10, 64.76, 52.76; MS (EI) 310.0 (M+). HRMS (EI) calcd for C$_{14}$H$_{14}$O$_4$S$_2$:310.0334. Found:310.0369.

EXAMPLE 20

3-(Hydroxymethyl)-6-[methyloxy[3-hydroxyquinoxalin-2-yl]]-1,2-dithiin.

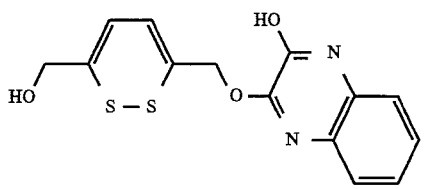

To a stirred solution of 3-(hydroxymethyl)-6-[(tert-butyldimethylsilyloxy)methyl]-1,2-dithiin (U.S. Ser. No. 08/212,096) (200 mg, 0.688 mmol) of in 2 mL dry THF was added a solution of 3-(tert-butyldimethylsilyloxy)-2-hydroxyquinoxaline obtained from the reaction of 2,3-dihydroxyquinoxaline with tert-butyldimethylsilyl chloride and imidazole as in Example 6 (248 mg, 1.753 mmol) in 2 mL THF, followed by addition of triphenylphosphine (220 mg, 0.839 mmol). The resulting solution was cooled to 0° C., then 140 μL (155 mg, 0.890 mmol) of diethylazodicarboxylate was added, and the reaction mixture was kept at 0°–5° C. for 2 h until TLC analysis showed the reaction to be complete. For isolation of the products, the reaction mixture poured directly onto a silica gel column and eluted with ethyl acetate-hexane, 1:6, to give 3-[(tert-butyldimethylsilyloxy)methyl]-6-[methyloxy[3-hydroxyquinoxalin-2-yl]]-1,2-dithiin (104 mg, 28.2%). No product of N-alkylation was isolated; MS (+LSIMS) 549.4 (MH+).

To a stirred solution of the 3-[(tert-butyldimethylsilyloxy)methyl]-6-[methyloxy[3-(tert-butyldimethylsilyloxy)quinoxalin-2-yl]]-1,2-dithiin obtained above (50 mg, 0.09 mmol) in 1 mL of THF was added a mixture of 1.2 mL of 1M tetrabutylammonium fluoride in THF and 0.7 mL of acetic acid. The reation mixture was stirred for 3 h until TLC analysis showed the reaction to be complete, and then concentrated in vacuo. The residue was partitioned between 20 mL of water and 30 mL of ethyl acetate. The organic phase was washed with dilute aqueous sodium bicarbonate, water, dried over sodium sulfate, and then evaporated to a small volume. The residue was purified by flash chromatography (ethyl acetate-hexane, 1:1) to yield 15 mg (51.7%) of the title compound. Further purification was accomplished by reverse phase HPLC (acetonitrile:water 1:1, PRP-1 column); $^1$H-NMR (CD$_3$OD) 5.68 (d, J=8.0, 1 H), 7.47 (m, 2 H), 7.37 (m, 1 H), 6.66 (d, J=5.6, 1 H), 6.42 (d, J=6.0, 1 H), 5.16 (s, 2 H), 4.17 (s, 2 H); MS (EI) 319.1 (M+).

EXAMPLE 21

3-(Hydroxymethyl)-6-[(2-chloro-5-trifluoromethyl-phenyloxy)methyl]-1,2-dithiin.

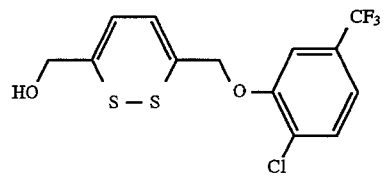

To a stirred solution of 3-(hydroxymethyl)-6-[(tert-butyldimethylsilyloxy)methyl]-1,2-dithiin (U.S. Ser. No. 08/212,096) (200 mg, 0.688 mmol) in 5 mL dry THF was added a solution of 2-chloro-5-(trifluoromethyl) phenol (271 mg, 180 μL, 1.38 mmol) in 5 mL of THF, followed by the addition of triphenylphosphine (220 mg, 0.83 mmol). The resulting solution was cooled to 0° C., then 140 μL (155 mg, 0.89 mmol) of diethylazodicarboxylate was added, and the reaction mixture was kept at 0°–5° C. for 30 min and then the ice-water bath was removed. The reaction mixture was stirred at rt for 17 h. For isolation of the products the reaction mixture was chromatographed directly on a silica gel column, using ethyl acetate-hexane (1:3) as eluant, to yield 3-[(tert-butyldimethylsilyloxy)methyl]-6-[(2-chloro-5-trifluoromethyl-phenyloxy)methyl]-1,2-dithiin, 200 mg (62%); $^1$H NMR(CDCl$_3$):δ7.54 (d, J=8, 1 H), 7.23 (d, J=8.4, 1 H), 7.16 (s, 1 H), 6.54 (d, J=6.4, 1 H), 6.42(d, J=6.4, 1 H), 4.78(s, 2 H), 4.31 (s, 2 H), 0.9 (s, 9 H), 0.1 (s, 6 H); MS (EI):m/z 468.1.

To a stirred solution of the 3-[(tert-butyldimethylsilyloxy)methyl]-6-[(2-chloro-5-trifluoromethyl-phenyloxy)methyl]-1,2-dithiin obtained above (290 mg, 0.62 mmol) in 8 mL of THF was added a solution of 4 mL of 1M tetrabutylammonium fluoride in THF and 2.5 mL of acetic acid. The reaction mixture was stirred for 5 h until TLC analysis showed the reaction to be complete. The reaction mixture was partitioned between 30 mL of water and 50 mL of ethyl acetate. The organic phase was washed with 3% aqueous sodium bicarbonate (50 mL). The aqueous layer was extracted with ethyl acetate (3×50 mL) and then the combined organic layer was washed with water, dried over magnesium sulfate and concentrated to a small volume. The residue was chromatographed over a silica gel column (ethyl acetate-hexane, 1:3) to yield 120 mg (57%) of the title compound as a yellow solid. The compound was further purified by reverse phase HPLC (PRP-1 column, acetonitrile:water gradient), mp 94.2°–96° C.; $^1$H NMR (CDCl$_3$):δ7.51 (d, J=8.4, 1 H), 7.22 (dd, J=6.8, J=2.0, 1 H), 7.16 (d, J=1.2, 1 H), 6.55 (d, J=6.0, 1 H), 6.5 (d, J=6.0, 1 H), 4.79 (s, 2 H), 4.31 (d, 2 H, J=5.6) 1.80 (t, J=6.0, 1 H); $^{13}$C NMR(CDCl$_3$):δ153.69, 136.86, 136.49, 130.98, 130.85, 128.30, 127.54, 124.77, 119.13, 118.28, 111.03, 70.73, 64.53, MS (EI):354 (M+). Anal. calcd for C$_{13}$H$_{10}$ClF$_3$O$_2$S$_2$:C, 44.01; H, 2.84. Found:C, 43.74; H, 2.94.

EXAMPLE 22

3-(Hydroxymethyl)-6-[methyloxy[methyl benzoate-4-yl]-1,2-dithiin.

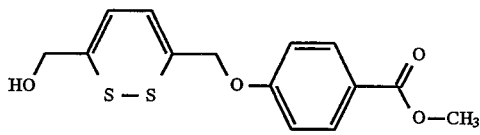

To a stirred solution of 3-(hydroxymethyl)-6-[(tert-butyldimethylsilyloxy)methyl]-1,2-dithiin (U.S. Ser. No. 08/212,096) (200 mg, 0.688 mmol) in 2 mL dry THF was added a solution of methyl 4-hydroxybenzoate (155 mg, 1.02 mmol) in 2 mL of THF, followed by the addition of triphenylphosphine (268 mg, 1.02 mmol). The resulting solution was cooled to 0° C., then 161 μL (178 mg, 1.02 mmol) of diethylazodicarboxylate was added, and the reaction mixture was kept at 0°–5° C. for 3 h until TLC analysis showed the reaction to be complete. For isolation of the products the reaction mixture was chromatographed directly on a silica gel column, using ethyl acetate-hexane (1:20) as eluant, to yield 3-[(tert-butyldimethylsilyloxy)methyl]-6-[methyloxy[methyl benzoate-4-yl]]-1,2-dithiin (70 mg, 23.9%); $^1$H-NMR (CDCl$_3$) 8.00 (d, J=8.8, 2 H), 6.95 (d, J=8.8, 2 H), 6.46 (d, J=6.4, 1 H), 6.39 (d, J=6.4, 1 H), 4.73 (s, 2 H), 4.31 (s, 2 H), 3.90 (s, 3 H), 0.92 (s, 9 H), 0.11 (s, 6 H); $^{13}$C—NMR (CDCl$_3$) δ166.66, 161.72, 136.47, 132.28, 131.42, 128.53, 127.26, 123.37, 114.48, 69.54, 64.76, 51.87, 25.75, 18.30, –5.42; MS (EI) 424.1 (M+).

To a stirred solution of the 3-[(tert-butyldimethylsilyloxy)methyl]-6-[methyloxy[methyl benzoate-4-yl]]-1,2-dithiin obtained above (70 mg, 0.16 mmol) in 1 mL of THF was added a solution of 2 mL of 1M tetrabutylammonium fluoride in THF and 1 mL of acetic acid. The reaction mixture was stirred for 3 h until TLC analysis showed the reaction to be complete, then it was concentrated in vacuo. The residue was partitioned between 40 mL of water and 60 mL of ethyl acetate. The organic phase was washed with dilute aqueous sodium bicarbonate, water, dried over sodium sulfate, and then evaporated to a small volume. The residue was chromatographed over silica gel column (ethyl acetate-hexane, 1:1) to yield 36 mg (70.5%) of the title compound; $^1$H-NMR (CD$_3$OD) δ7.95 (d, J=6.8, 2 H), 7.02 (d, J=6.8, 2 H), 6.52 (d, J=6.0, 1 H), 6.41 (d, J=6.0, 1 H), 4.78 (s, 2 H), 4.19 (s, 2 H), 3.86 (s, 3 H); $^{13}$C—NMR (CD$_3$OD) δ168.28, 163.50, 138.28, 132.56, 130.17, 128.99, 125.41, 124.24, 115.78, 70.82, 64.70, 52.40; MS (EI) 310.0 (M+). HRMS (EI) calcd for C$_{14}$H$_{14}$O$_4$S$_2$:310.0334, found:310.0354.

EXAMPLE 23

2-[tert-Butyldimethysilyloxy]-3-fluorophenol and 1-[tert-Butyldimethysilyloxy]-3-fluorophenol.

3-Fluorocatechol (800 mg, 6.25 mmol) was dissolved in anhyd. DMF (20 mL) and then imidazole (850 mg, 12.5 mmol) was added, followed by the slow addition of a premixed solution of tert-butyldimethylsilyl chloride (942 mg, 6.25 mmol) in DMF (10 mL) at rt. The reaction mixture was stirred at rt for 17 h. The reaction mixture was partitioned between ether (50 mL) and water (30 mL), and then the separated layer was washed with water. After drying (MgSO$_4$) and concentration by rotary evaporation, the residue was purified by chromatography (silica gel, ethyl acetate-hexane, 1:3), yielding 730 mg (48%) of the mixture of the title compounds, which were inseparable by chromatography and used directly for the subsequent step; $^1$H NMR (CDCl$_3$) δ6.9–6.6 (m, 6 H), 5.3 (bs, 2 H), 1.04 (s, 9 H), 1.03 (s, 9 H), 0.28 (s, 6 H), 0.27 (s, 3 H), 0.26 (s, 3 H); MS (EI) 242.1 (M+).

EXAMPLE 24

3-(Hydroxymethyl)-6-[(2-hydroxy-3-fluoro-phenyloxy-1-yl) methyl]-1,2-dithiin(G) and 3-(Hydroxymethyl)-6-[(1-hydroxy-3-fluoro-phenyloxy-2-yl)methyl]-1,2-dithiin(H).

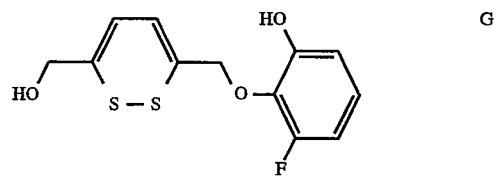

-continued

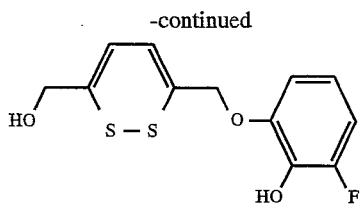

To a stirred solution of 3-(hydroxymethyl)-6-[(tert-butyldimethylsilyloxy)methyl]-1,2-dithiin (U.S. Ser. No. 08/212,096) (300 mg, 1.10 mmol) in 7 mL dry THF was added a solution of a mixture of the 2-[tert-butyldimethysilyloxy]-3-fluorophenol and 1-[tert-butyldimethysilyloxy]-3-fluorophenol obtained from Example 23 (500 mg, 2.20 mmol) in 7 mL of THF, followed by the addition of triphenylphosphine (260 mg, 1.65 mmol). The resulting solution was cooled to 0° C., then 160 µL (177 mg, 1.65 mmol) of diethylazodicarboxylate was added, and the reaction mixture was kept at 0°–5° C. for 30 min and then stirred at rt for 4 h, during which time the starting material disappeared. For isolation of the products the reaction mixture was chromatographed, directly on a silica gel column, using ethyl acetate-hexane (1:6) as eluant, to yield a mixture of two products, 3-[(tert-butyldimethylsilyloxy)methyl]-6-[(2-hydroxy-3-fluorophenyloxy-1-yl)methyl]-1,2-dithiin and 3-[(tert-butyldimethylsilyloxy)methyl]-6-[(1-hydroxy-3-fluorophenyloxy-2-yl)methyl]-1,2-dithiin (300 mg, 56%); MS (EI) :m/z 514.

To a stirred solution of the mixture of 3-[(tert-butyldimethylsilyloxy)methyl]-6-[(2-hydroxy-3-fluorophenyloxy-1-yl)methyl]-1,2-dithiin and 3-[(tert-butyldimethylsilyloxy)methyl]-6-[(1-hydroxy-3-fluorophenyloxy-2-yl)methyl]-1,2-dithiin obtained above (300 mg, 0.58 mmol) in 10 mL of THF was added a solution of 6 mL of 1M tetrabutylammonium fluoride in THF and 3.6 mL of acetic acid. The reaction mixture was stirred for 20 h at rt during which time TLC analysis showed the reaction to be complete. The residue was partitioned between 30 mL of water and 50 mL of ethyl acetate. The organic phase was washed with 3% aqueous sodium bicarbonate. The aqueous layer was extracted with ethyl acetate (2×50 mL), and then the combined ethyl acetate layers were dried over magnesium sulfate, and then concentrated to a small volume. The residue was chromatographed over a silica gel column (ethyl acetate-hexane, 1:1) to yield 120 mg (72%) of the two title compounds. The compounds were inseparable by reverse-phase HPLC (PRP-1 column, acetonitrile:water gradient, mp of mixture 67.5°–69.4° C.; $^1$H NMR (CDCl$_3$):δ6.96–6.6 (m, 6 H), 6.48–6.35 (m, 4 H), 4.78 (s, 2 H), 4.76 (s, 2 H), 4.31 (s, 2 H), 4.29 (s, 2 H); MS (EI):286 (M+).

EXAMPLE 25

3-(Hydroxymethyl)-6-[methylthio-[1-(4-hydroxyphenyl)tetrazol-5-yl]]-1,2-dithiin.

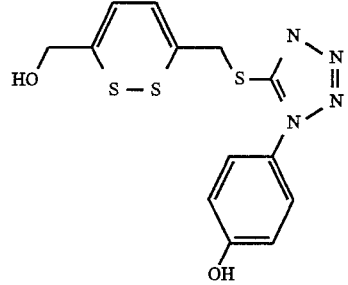

To a stirred solution of 3-(hydroxymethyl)-6-[(tert-butyldimethylsilyloxy)methyl]-1,2-dithiin (U.S. Ser. No. 212,096) (600 mg, 2.07 mmol) in 6 mL of dry THF was added a solution of 4-hydroxyphenyl-1H-tetrazole-5-thiol (obtained from the Aldrich Chemical Co.) (594 mg, 3.07 mmol) in 6 mL of THF, followed by addition of triphenylphosphine (804 mg, 3.07 mmol). The resulting solution was cooled to 0° C., then 483 µL (534 mg, 3.07 mmol) of diethylazodicarboxylate was added, and the reaction mixture was kept at 0°–5° C. for 1 h until TLC analysis showed the reaction to be complete. For isolation of the products the reaction mixture was chromatographed directly on a silica gel column, using ethyl acetate-hexane, 1:3, to yield 480 mg (51.5%) of 3-[(tert-butyldimethylsilyloxy)methyl]-6-[methylthio-[1-(4'-hydroxyphenyl)-tetrazol-5-yl]]-1,2-dithiin; $^1$H-NMR (CD$_3$OD) δ7.36 (d, J=8.0, 2 H), 6.96 (d, J=8.0, 2 H), 6.46 (d, J=6.0, 1 H), 6.31 (d, J=6.42 1 H), 4.28 (s, 2 H), 4.24 (s, 2 H), 0.90 (s, 9 H), 0.09 (s, 6 H); $^{13}$C—NMR (CD$_3$OD) δ160.97, 154.94, 137.65, 130.27, 129.53, 127.46, 126.15, 125.53, 117.33, 66.13, 40.11, 26.33, 19.22, −5.18. MS (+FAB) 466.0 (M+).

To a stirred solution of the 3-[(tert-butyldimethylsilyloxy)methyl]-6-[methylthio-[1-(4-hydroxyphenyl)-tetrazol-5-yl]]-1,2-dithiin obtained above (440 mg, 0.94 mmol) in 4 mL of THF was added a solution of 7 mL of 1M tetrabutylammonium fluoride in THF and 4 mL of acetic acid. The reaction mixture was stirred for 1 h at 0° C. until TLC analysis showed the reaction to be complete, then concentrated in vacuo. The residue was partitioned between 60 mL of water and 90 mL ethyl acetate. The organic phase was washed with dilute aqueous sodium bicarbonate, water, dried over sodium sulfate, and then concentrated to a small volume. The residue was purified by flash chromatography (ethyl acetate-hexane, 1:3) to yield 265 mg (79.8%) of the title compound as yellow crystals, mp 130°–131° C.; $^1$H-NMR (CD$_3$OD) δ7.36 (d, J=9.2, 2 H), 6.97 (d, J=9.2, 2 H), 6.47 (d, J=6.0, 1 H), 6.34 (d, J=6.4, 1 H) 4.24 (s 2 H), 4.15 (s, 2 H); $^1$H-NMR (DMSO-d$_6$):10.26 (s, 1 H, phenol OH), 7.41 (d, 2 H, J=8.8), 6.97 (d, 2 H, J=8.8), 6.52 (d, 1 H, J=6.0), 6.35 (d, 1 H. J=6.0), 5.39 (t, 1 H, J=5.2), 4.30 (s, 2 H), 4.06 (d, 2 H, J=5.2); $^{13}$C—NMR (CD$_3$OD) δ160.99, 154.90, 138.09, 130.34, 129.49 127.42, 126.05, 125.77, 117.29, 64.67, 40.01; $^1$H-NMR NOESY showed an interaction between aromatic and dithiin rings protons. MS (+FAB) 353.5 (MH+

); IR (KBr) 3378.7 (OH); 3135 (OH)cm$^{-1}$. HMBC (DMSO-d$_6$) shows a long range correlation between the protons at 4.30 ppm and the carbon at 154.90 ppm. Anal. calcd for C$_{13}$H$_{12}$N$_4$O$_2$S$_3$:C, 44.30; H, 3.43; N, 15.90; S, 27.29. Found:C, 44.68; H, 3.37; N, 16.24; S, 27.23.

EXAMPLE 26

3-(Hydroxymethyl)-6-1[4-(imidazol-1-yl)phenyloxy)methyl]]-1,2-dithiin.

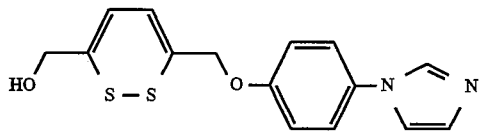

To a stirred solution of 3-(hydroxymethyl)-6-[(tert-butyldimethylsilyloxy)methyl]-1,2-dithiin (U.S. Ser. No. 08/212,096) (300 mg, 1.04 mmol) in 3 mL of dry THF was added a solution of 4-(imidazol-1-yl)phenol (250 mg, 1.56 mmol) in a mixture of 3 mL THF and 3 mL DMF, followed by the addition of triphenylphosphine (402 mg, 1.50 mmol). The resulting solution was cooled to 0° C., 242 μL (267 mg, 1.50 mmol) of diethylazodicarboxylate was added, and then the reaction mixture was kept at 0°–5° C. for 3 hour until TLC analysis showed the reaction to be complete. For isolation of the products, the reaction mixture was chromatographed directly on a silica gel column, using ethyl acetate-hexane, 1:1, to give 330 mg of a yellow residue, which contained the desired product plus some triphenylphosphine oxide. The crude residue was dissolved in 3 mL THF and a solution of 7 mL of 1M tetrabutylammonium fluoride in THF and 4 mL of acetic acid was added. The reation mixture was stirred for 3 h at rt until TLC analysis showed the reaction to be complete. After concentration in vacuo, the residue was partitioned between 60 mL of water and 90 mL of ethyl acetate. The organic phase was washed with dilute aqueous sodium bicarbonate, water, dried over sodium sulfate, and then concentrated to a small volume. The residue was purified by chromatography over a silica gel column (ethyl acetate-hexane, 1:1) to afford 66 mg (20.1%) of the title compound as yellow crystals, mp 122°–124° C.; $^1$H-NMR (CD$_3$OD) δ8.02 (s, 1 H), 7.48 (d J=3.6, 2 H), 7.46 (s, 1 H), 7.12 (d, J=3.2, 2 H), 7.10 (s, 1 H), 6.53 (d, J=6.4, 1 H), 6.41 (d, J=6.4, 1 H), 4.78 (s, 2 H), 4.19 (s, 2 H); $^{13}$C—NMR (CD$_3$OD) δ159.01, 138.18, 137.02 132.45, 130.60, 129.93, 128.89, 125.41, 124.03, 120.14, 117.38, 71.19, 64.71.

EXAMPLE 27

3-(Hydroxymethyl)-6-[[(2,2-dimethyl-1,3-dioxolan-4-yl)methyloxy]methyl]-1,2-dithiin (I) and 3,6-Bis[[(2,2-dimethyl-1,3-dioxolan-4-yl)methyloxy]methyl]-1,2-dithiin (J).

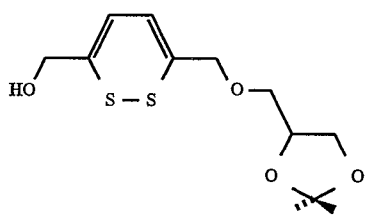

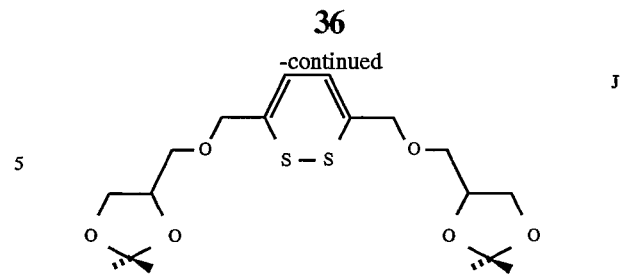

To a stirred solution of 330 mg (1.87 mmol) of 3,6-Bis(hydroxymethyl)-1,2-dithiin (U.S. Ser. No. 08/212,096) in 8 mL of THF was added in portions at rt, 60% NaH (160 mg, 4.00 mmol). After 15 min freshly prepared solution of 1-trifluoromethanesulfonyl-2,3-O-isopropylidine glycerol [1.8 g, 6.82 mmol, (prepared according to the method of Tempesta, M.; Jolad, S. D.; King, S.; Mao, G.; Bruening, R. C.; Truong, T. V.; Bierer, D. E. WO 9408563] in 2 mL of THF was added dropwise. After 3 h at rt TLC showed two new spots at Rf 0.36 and 0.51 (EtOAc:hexane, 1:1) along with starting material. The reaction mixture was quenched with 10 mL of methanol, concentrated to a small volume, and then separated on a silica gel column (EtOAc-hexane, 1:3) to yield 144 mg (29.1%) of monoaddition product, 3-(hydroxymethyl)-6-[[(2,2-dimethyl-1,3-dioxolan-4-yl) methyloxy]methyl]-1,2-dithiin, 247 mg (35.9%) of the diaddition product, 3,6-Bis[[(2,2-dimethyl-1,3-dioxolan-4-yl)methyloxy]methyl]-1,2-dithiin, both as orange oils, and 27 mg (8.2%) of starting the starting dithiin diol.

In the case that 100 mol % of NaH was used in this reaction under the same conditions, the recovery of starting dithiin diol was 33.3%, and the yields of the monoadduct and diadduct were 20.4%, and 2.5% respectively.

Characterization of 3-(hydroxymethyl)-6-[[(2,2-dimethyl-1,3-dioxolan-4-yl)methyloxy]methyl]-1,2-dithiin: 1 H-NMR (CDCl$_3$) δ6.36 (dd, J=6.4, J=6.4, 2 H), 4.32–4.23 (m, 3 H), 4.20 (d, J=5.2, 2 H), 4.07 (dd, J=6.4, J=6.8, 1 H), 3.77 (dd, J=6.4, J=6.4, 1 H), 3.58–3.48 (m, 2 H), 2.16 (bt, 1 H), 1.43 (s, 3 H), 1.36(s, 3 H); $^{13}$C—NMR (CDCl$_3$) δ135.35, 131.95, 126.75, 124.84, 109.49, 74.54, 72.97, 70.96, 66.63, 64.49, 26.70, 25.32; MS (EI) 290.2 (M+). HRMS (EI) calcd for C$_{12}$H$_{18}$O$_4$S$_2$:290.0647, found:290.0629.

Characterization of 3,6-Bis[[(2,2-dimethyl-1,3-dioxolan-4-yl)methyloxylmethyl]-1,2-dithiin: $^1$H-NMR (CDCl$_3$) δ6.33 (s, 2 H), 4.29 (p, J=5.6, J=6.0, 2 H), 4.15 (dd, J=13.2, J=13.2, 4 H), 4.07 (dd, J=6.41, J=6.4, 2 H), 3.72 (dd, J=6.4, J=6.4 2 H), 3.47 (dddd, J=5.6, J=5.6, J=5.2 J=5.2, 4 H), 1.39 (s, 6 H), 1.32 (s, 6 H); $^{13}$C—NMR (CDCl$_3$) δ132.34, 126.45, 109.42, 74.49, 72.88, 70.97, 66.59, 26.66, 25.28; MS (EI) 404.3 (M+). HRMS calcd for C$_{18}$H$_{28}$O$_6$S$_2$:404.1327, found 404.1303.

EXAMPLE 28

3-(Hydroxymethyl)-6-[methyloxy(2,3-dihydroxypropane-1-yl)]-1,2-dithiin.

3-(Hydroxymethyl)-6-[[(2,2-dimethyl-1,3-dioxolan-4-yl) methyloxy]methyl]-1,2-dithiin obtained from Example 27

(105 mg, 0.36 mmol) was dissolved in 6 mL 60% ACOH and the solution was allowed to stir 4 h at rt, and then it was partitioned between 30 mL of water and 50 mL of ethyl acetate. The separated organic phase was washed with dilute aqueous sodium bicarbonate, water, dried over sodium sulfate, and then concentrated to a small volume. The residue was purified by chromatography (silica gel, ethyl acetate) to yield 39.6 mg (43.7%) of the title compound as an orange oil, $R_f$ 0.27 (EtOAc); $^1$H-NMR (CD$_3$OD) δ6.39 (d, J=6.4, J=6.4, 2 H), 4.18 (s, 5 4 H), 3.73 (p, 1 H), 3.61–3.44 (m, 4 H); $^{13}$C—NMR (CD$_3$OD) δ137.21, 132.81, 128.11, 125.54, 73.89, 72.59, 72.20, 64.76, 64.48; MS (EI) 250.1 (M+). HRMS (EI) calcd for C$_9$H$_{14}$O$_4$S$_2$:250.0333, found:250.00329.

EXAMPLE 29

3-[[(2,2-Dimethyl-1,3-dioxolan-4-yl)methyloxy]methyl]-6-[methyloxy(2,3-dihydroxypropane-1-yl)]-1,2-dithiin.

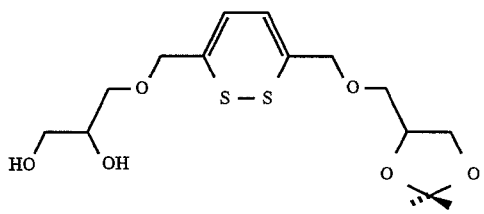

3,6-Bis[[(2,2-dimethyl-1,3-dioxolan-4-yl)methyloxy]methyl]-1,2-dithiin obtained in Example 27 (80 mg, 0.19 mmol) was dissolved in 5 mL of 60% AcOH and the solution was allowed to stir 2 h at rt; then it was partitioned between 30 mL of water and 50 mL of ethyl acetate. The organic phase was washed with dilute aqueous sodium bicarbonate, water, dried over sodium sulfate, and then concentrated to a small volume. The residue was purified by chromatography (silica gel, ethyl acetate) to yield 15 mg (20.8%) of the title compound as an orange oil, $R_f$ 0.32 (EtOAc); $^1$H-NMR (CD$_3$OD) δ6.41 (s, 2 H), 4.26 (p, 1 H)) 4.19 (d, J=4.4, 4 H), 4.05 (t, J=6.4, 1 H), 3.79–3.72 (m, 2 H), 3.61–3.44 (m, 6 H), 1.38 (s, 3 H), 1.32 (s, 3 H); $^{13}$C—NMR (CD$_3$OD) δ134.01, 133.54, 128.16, 127.82, 110.61, 76.10, 73.90, 73.84, 72.71, 72.26, 71.96, 67.59, 64.51, 27.05, 25.66; MS (EI) 364.1 (M+). HRMS (EI) calcd for C$_{15}$H$_{24}$O$_6$S$_2$:364.1014, found:364.1027.

EXAMPLE 30

3-(Hydroxymethyl)-6-[methyloxy[methyl benzoate-2-yl]]-1,2-dithiin

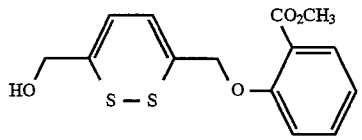

To stirred solution of 3-(hydroxymethyl)-6-[(tert-butyldimethylsilyloxy)methyl]-1,2-dithiin (U.S. Ser. No. 08/212,096) (216 mg, 0.744 mmol) in dry THF (0.34–0.8M) was added methyl salicylate (200 μl, 235 mg, 1.54 mmol) in THF (0.4–1.2M), followed by triphenylphosphine (240 mg, 1.09 mmol). The solution was cooled to 5° C. whereupon diethylazodicarboxylate (144 mg, 0.827 mmol) was added. The reaction mixture was allowed to warm to room temperature over 5.5 h, applied directly to a silica gel column and purified (EtOAc/hexane (1/7) to give 265 mg of 3-[(tert-butyldimethylsilyloxy)methyl]-6-[methyloxy[methyl benzoate-2-yl]]-1,2-dithiin.

To a solution of the 3-[(tert-butyldimethylsilyloxy)methyl]-6-[methyloxy[methyl benzoate-2-yl]]-1,2-dithiin (265 mg) obtained above in acetonitrile (0.2–0.3M) cooled to 0° C. was added a premixed solution of aqueous HF (1 mL) and acetonitrile (3 mL). The solution was allowed to stir for 45–60 min in an ice bath. The reaction mixture was neutralized with aqueous 10% K$_2$CO$_3$ (approx 25 mL) until evolution of CO$_2$ ceased. This solution was diluted with saturated NaCl (25 mL) and extracted with EtOAc (2×50 mL). The combined EtOAc layers were washed with saturated aqueous NaCl (2×50 mL), dried (Na$_2$SO$_4$), and concentrated in vacuo. Purification of the residue by chromatography using EtOAc-hexane (1:7) yielded 64.3 mg (28%) of the title compound; $^1$H NMR (CDCl$_3$) δ7.74 (d, J=7.6, 1 H), 7.48 (t, J=7.6, 1 H), 7.08 (d, J=8.8, 1 H), 7.03 (t, J=8.0, 1 H), 6.56 (d, J=5.6, 1 H), 6.41 (d, J=6.0, 1 H), 4.76 (s, 2 H), 4.19 (s, 2 H), 3.85 (s, 3 H); $^{13}$C NMR (CDCl$_3$) δ168.59, 158.79, 138.02, 134.77, 132.53, 130.32, 128.52, 125.55, 122.25, 115.54, 71.61, 64.81, 52.63; MS (LSIMS) 310 (M+). HRMS (EI) calcd for C$_{14}$H$_{14}$O$_4$S$_2$:310.0334, found:310.0355.

EXAMPLE 31

3-(Benzoyloxymethyl)-6-(hydroxymethyl)-1,2-dithiin.

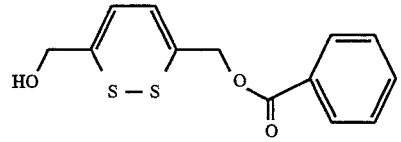

To a solution of triethylamine (2.0 mL, 14.3 mmol) in THF (5 mL) cooled to −10° C. was added benzoyl chloride (0.10 g, 0.71 mmol) followed by 3-(hydroxymethyl)-6-[tert-butyldimethylsilyloxy)methyl]-1,2-dithiin (U.S. Ser. No. 08/212,096) (200 mg, 0.688 mmol) in one portion. The reaction mixture was allowed to stir at −10° to −5° C. for 1 h. The reaction mixture was partitioned between ether and cold 1M H$_3$PO$_4$. The separated organic layer was washed with water, dried and concentrated. Purification by chromatography, eluting with EtOAc/hexane (1/3) yielded 0.25 g (92.5%) of 3-[(tert-butyldimethysilyloxy)methyl]-6-(benzoyloxymethyl)-1,2-dithiin.

To a stirred solution of the 3-[(tert-butyldimethysilyloxy)methyl]-6-(benzoyloxymethyl)-1,2-dithiin (250 mg, 0.63 mg) obtained above in THF (0.2–0.3M) was added a premixed solution of tetrabutylammonium fluoride (TBAF, 800–1250 mol % of a 1M solution in THF) and acetic acid (1.75-2:1, v/v, 1M TBAF/HOAc) at room temperature. The mixture was stired for 1–4 h. The solvent was concentrated and the residue was partitioned between water (40 mL) and EtOAc (60 mL). The organic phase was washed with dilute aqueous NaHCO$_3$ (50 mL), water (50 mL), dried (Na$_2$SO$_4$), and concentrated to a small volume. Purification was done by chromatography, eluting with EtOAc/hexane mixtures, to yield 94 mg of the title compound (53.4%); $^1$H NMR (CDCl$_3$) δ8.08–8.05 (m, 2 H), 7.57 (dd, J=7.2, 8.0, 1 H), 7.48–7.39 (m, 2 H), 6.47 (d, J=6.0, 1 H), 6.40 (d, J=6.0, 1 H), 4.96 (s, 2 H), 4.28 (s, 2 H), 2.2 (bs); MS 280.0 (M+).

DISINFECTANT OR CLEANING COMPOSITIONS COMPRISING A 1,2-DITHIIN COMPOUND

EXAMPLE 32

A rag, sponge or mop is saturated with a composition containing 25% isopropyl alcohol, 1% sodium dodecylsulfate, 0.01% 3-(hydroxymethyl)-6-[(pyridyl-2-oxy-1-yl)methyl]-1,2-dithiin and 73.99% distilled water. The floor of a bathroom which was used by a person having a fungal infection and is thus contaminated with the fungus is wiped with the rag, sponge or mop containing the above composition. The resulting bathroom floor is now disinfected and ready for use. The resulting floor may optionally be washed with detergent prior to use, if desired.

EXAMPLE 33

Approximately 10 mL of a composition containing 25% isopropyl alcohol, 1% sodium dodecylsulfate, 0.01% 3-(hydroxymethyl)-6-[(2-fluorophenyloxy)methyl]-1,2-dithiin and 73.99% distilled water are poured into a laboratory flask which contains a live culture of Candida albicans fungus. The flask is swerled several times and allowed to sit at room temerature for a short period of time. The contents of the flask are discarded, the flask is rinsed with sterile water and the flask is allowed to air dry under aseptic conditions. The resulting flask is now disinfected and ready for re-use. The resulting flask may optionally be washed with soap and water prior to re-use, if desired.

EXAMPLE: ANTIFUNGAL EFFECTS OF 1,2-DITHIIN COMPOUNDS

The following experiments demonstrate that representative 1,2-dithiin compounds of the present invention produce a significant and consistent antifungal effect as determined in an in vitro assay.

The antifungal activities of representative 1,2-dithiin compounds listed below were determined in vitro using three fungal cultures: *Candida albicans* ATCC10259 (CA), *Cryptococcus neoformans* ATCC36556 (CN), and *Aspergillus fumigatus* ATCC13073 (AF). The the minimum inhibitory concentration (MIC) for each 1,2-dithiin compound is shown below in Table I.

The method used to determine in vitro antifungal activity is discussed in McGinnis, M. R., *Laboratory Handbook of Medical Mycology*, Academic Press, New York, London, p 661 (1980); and Drouget, E.; Dupont, B.; Improvist, L.; Vivian, M. A.; and Tortorano, A. M.; "Disc Agar Diffusion and Microplate Automatized Techniques for In Vitro Evaluation of Antifungal Agents on Yeast and Sporulated Pathogenic Fungi" in In Vitro and In Vivo Evaluation of Antifungal Agents, Eds. Iwata, K. and Vanden Bossche, H., Elsevier Science Publishers, New York, Oxford, p. 303 (1986).

The abbreviations used for the various fungi in Table I are as follows:

| Fungi | Abbreviation |
| --- | --- |
| *Candida albicans* ATCC10259 | (CA) |
| *Cryptococcus neoformans* ATCC36556 | (CN) |
| *Aspergillus fumigatus* ATCC13073 | (AF) |

TABLE I

Minimum Inhibitory Concentration of Representative 1,2-Dithiin Compounds on CA, CN and AF Fungal Cultures

| 1,2-Dithiin Derivative | MIC (μg/mL) | | |
| --- | --- | --- | --- |
| | CA | CN | AF |
| 3-(Hydroxymethyl)-6-[(phenyloxy)methyl]-1,2-dithiin | 25 | 12.5 | 25 |
| 3-(Hydroxymethyl)-6-[(pyridyl-2-oxy-1-yl)methyl]-1,2-dithiin | 3.1 | 3.1 | 3.1 |
| 3-(Hydroxymethyl)-6-[(pyrid-2-one-1-yl)methyl]-1,2-dithiin | >100 | 12.5 | >100 |
| 3-(Hydroxymethyl)-6-[(pyridyl-3-oxy)methyl]-1,2-dithiin | 3.1 | 1.6 | 3.1 |
| 3-(Hydroxymethyl)-6-[(3-hydroxyphenyloxy)methyl]-1,2-dithiin | 50 | 100 | >100 |
| 3-(Hydroxymethyl)-6-[[3-(N,N-dimethylamino)phenyloxy]methyl]-1,2-dithiin | >50 | 50 | 100 |
| 3-(Hydroxymethyl)-6-[(3-hydroxypyridazin-6-one-1-yl)methyl]-1,2-dithiin | >100 | >100 | >100 |
| 3-(Hydroxymethyl)-6-[(3-hydroxypyridazine-6-oxy)methyl]-1,2-dithiin | >100 | >100 | >100 |
| 3-(Hydroxymethyl)-6-[(2-trifluoromethylphenyloxy)methyl]-1,2-dithiin | 25 | 6.3 | 50 |
| 3-(Hydroxymethyl)-6-[(2-fluorophenyloxy)methyl]-1,2-dithiin | 3.1 | 1.6 | 3.1 |
| 3-(Hydroxymethyl)-6-[(5-nitropyridyl-2-oxy)methyl]-1,2-dithiin | 0.2 | 0.1 | 0.4 |
| 3-(Hydroxymethyl)-6-[(5-nitropyrid-2-one-1-yl)methyl]-1,2-dithiin | >100 | 100 | >100 |
| 3-(Hydroxymethyl)-6-[(3-ethynylphenyloxy)methyl]-1,2-dithiin | 1.6 | 1.6 | 6.3 |
| 3-(Hydroxymethyl)-6-[methyloxy[methyl benzoate-3-yl]]-1,2-dithiin | 3.1 | 6.3 | 25 |
| 3-(Hydroxymethyl)-6-[methyloxy[3-hydroxyquinoxalin-2-yl]]-1,2-dithiin | 50 | 25 | 100 |
| 3-(Hydroxymethyl)-6-[(2-chloro-5-trifluoromethyl-phenyloxy)methyl]-1,2-dithiin | 1.6 | 1.6 | 6.3 |
| 3-(Hydroxymethyl)-6-[methyloxy[methyl benzoate-4-yl]]-1,2-dithiin | 3.1 | 3.1 | 12.5 |
| 3-(Hydroxymethyl-6-[(2-hydroxy-3-fluoro-phenyloxy)methyl]-1,2-dithiin and 3-(Hydroxymethyl)-6-[(1-hydroxy-3-fluoro-phenyloxy)methyl]-1,2-dithiin | 12.5 | 6.3 | 12.5 |
| 3-(Hydroxymethyl)-6-[methylthio-[1-(4-hydroxyphenyl)-tetrazol-5-yl]]-1,2-dithiin | 25 | 6.3 | 12.5 |
| 3-(Hydroxymethyl)-6-[[4-(imidazol-1-yl)phenyloxy]-methyl]-1,2-dithiin | 12.5 | 100 | 100 |
| 3-(Hydroxymethyl)-6-[[2,2-dimethyl-1,3-dioxolan-4-yl)methyloxy]methyl]-1,2-dithiin | >100 | >100 | >100 |
| 3,6-Bis[[2,2-dimethyl-1,3-dioxolan-4-yl)methyloxy]methyl]-1,2-dithiin | >100 | >100 | >100 |
| 3-(Hydroxymethyl)-6-[methyloxy(2,3-dihydroxypropane-1-yl)-1,2-dithiin | >100 | >100 | >100 |
| 3-[[(2,2-Dimethyl-1,3-dioxolan-4-yl)methyloxy]methyl]-6-[methyloxy(2,3-dihydroxyropane-1-yl)]-1,2-dithiin | >100 | >100 | >100 |
| 3-(Hydroxymethyl)-6-[methyloxy(methyl benzoate-2-yl)]-1,2-dithiin | 6.3 | 6.3 | 12.5 |
| 3-(Benzoyloxymethyl)-6-(hydroxymethyl)-1,2-dithiin | 6.3 | 3.1 | 3.1 |

The results shown in Table I clearly demonstrate that the novel 1,2-dithiin compounds of the present invention possess antifungal activity against a variety of fungal cultures.

The present invention is not to be limited in scope by the specific embodiments disclosed in the examples which are intended as illustrations of a number of aspects of the invention and any embodiments which are functionally equivalent are within the scope of this invention. Indeed, various modifications of the invention in addition to those shown and described herein will become apparent to those skilled in the art and are intended to fall within appended claims.

A number of references have been cited, the entire disclosures of which are incorporated herein by reference.

What is claimed is:

1. A compound having the formula:

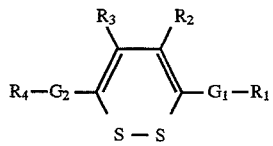

and pharmaceutically acceptable salts thereof, wherein:

$R_2$ and $R_3$ are hydrogen;

$G_1$ and $G_2$ are independently selected from the group consisting of a $C_1-C_{10}$ alkyl or branched alkyl group and a $C_3-C_{10}$ cycloalkyl group;

$R_1$ is —OH;

$R_4$ is selected from the group consisting of, —$OR_5$, —$O(CO)R_5$, —$SR_6$ and a pyridone radical of the type:

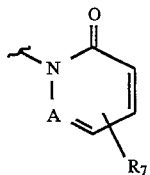

wherein $R_7$ is selected from the group consisting of hydrogen, —OH, —SH, —$NO_2$, —$NH_2$, halogen, trifluoromethyl, —CHO, —COOH, —$COOR_8$, —$OR_8$ and $SR_8$;

A is nitrogen or carbon;

$R_8$ is an alkyl group of 1 to 6 carbon atoms;

$R_5$ and $R_6$ are independently selected from the group consisting of a $C_1-C_{20}$ alkyl group, a $C_1-C_{20}$ alkenyl group, a $C_3-C_{10}$ cycloalkyl group and a radical of the type:

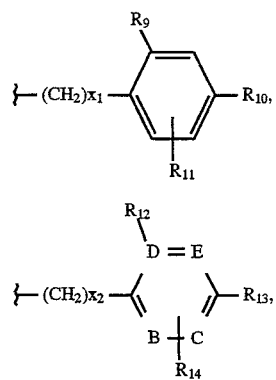

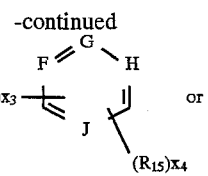

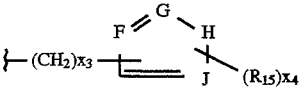

said $C_1-C_{20}$ alkyl and $C_1-C_{20}$ alkenyl group being optionally substituted with one or more $C_1-C_{20}$ alkyl groups;

$X_1$, $X_2$, $X_3$ and $X_4$ are independently 0–6;

$R_9$ is selected from the group consisting of hydrogen, a $C_1-C_6$ alkyl group, a $C_2-C_6$ alkenyl group, a $C_2-C_6$ alkynyl group, halogen, trifluoromethyl, trichloromethyl, tribromomethyl, —$NO_2$, —$NH_2$, —OH, —SH, —CHO and —COOH;

$R_{10}$ is selected from the group consisting of hydrogen, a $C_1-C_6$ alkyl group, a $C_2-C_6$ alkenyl group, a $C_2-C_6$ alkynyl group, halogen, trifluoromethyl, trichloromethyl, tribromomethyl, —$NO_2$, —$NH_2$, —OH, —SH, —CHO, —COOH, —$NR_{16}R_{17}$, —$OR_{18}$, —$SR_{19}$, —$COOR_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl groups being optionally substituted with one or more halogen, —$OCH_3$ or $C_1-C_6$ alkyl groups;

$R_{11}$ is selected from the group consisting of hydrogen, a $C_1-C_6$ alkyl group, a $C_2-C_6$ alkenyl group, a $C_2-C_6$ alkynyl group, halogen, trifluoromethyl, trichloromethyl, tribromomethyl, —$NO_2$, —$NH_2$, —OH, —SH, —CHO, —COOH, —$NR_{16}R_{17}$, —$OR_{18}$, —$SR_{19}$, —$COOR_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl groups being optionally substituted with one or more halogen, —$OCH_3$ or $C_1-C_6$ alkyl groups;

$R_{12}$ is selected from the group consisting of hydrogen, a $C_1-C_6$ alkyl group, a $C_2-C_6$ alkenyl group, a $C_2-C_6$ alkynyl group, halogen, trifluoromethyl, trichloromethyl, tribromomethyl, —$NO_2$, —$NH_2$, —OH, —SH, —CHO and —COOH;

$R_{13}$ is selected from the group consisting of hydrogen, a $C_1-C_6$ alkyl group, a $C_2-C_6$ alkenyl group, a $C_2-C_6$ alkynyl group, halogen, trifluoromethyl, trichloromethyl, tribromomethyl, —$NO_2$, —$NH_2$, —OH, —SH, —CHO, —COOH, —$NR_{16}R_{17}$, —$OR_{18}$, —$SR_{19}$, —$COOR_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl groups being optionally substituted with one or more halogen, —$OCH_3$ or $C_1-C_6$ alkyl groups;

$R_{14}$ is selected from the group consisting of hydrogen, a $C_1-C_6$ alkyl group, a $C_2-C_6$ alkenyl group, a $C_2-C_6$ alkynyl group, halogen, trifluoromethyl, trichloromethyl, tribromomethyl, —$NO_2$, —$NH_2$, —OH, —SH, —CHO, —COOH, —$NR_{16}R_{17}$, —$OR_{18}$, —$SR_{19}$, —$COOR_{20}$, phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl; said phenyl, pyridyl, pyrazinyl, imidazolyl, pyrimidyl, triazyl, triazolyl, thiadiazolyl, tetrazolyl, thiazolyl, thiatriazolyl, pyrrolyl, furanyl, and thiopheneyl groups being optionally substituted with one or more halogen, —$OCH_3$ or $C_1$–$C_6$ alkyl groups;

$R_{15}$ is selected from the group consisting of hydrogen, a $C_1$–$C_6$ alkyl group, a $C_2$–$C_6$ alkenyl group, a $C_2$–$C_6$ alkynyl group, halogen, trifluoromethyl, trichloromethyl, tribromomethyl, —$NO_2$, —$NH_2$, —OH, —SH, —CHO, —COOH, —$COOR_{25}$, and phenyl; said phenyl being optionally substituted with one or more halogens, —$OCH_3$ or $C_1$–$C_6$ alkyl groups;

$R_{16}$ and $R_{17}$ are independently a $C_1$–$C_6$ alkyl group or form together a ring of 3 to 8 carbon atoms;

$R_{18}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, an alkyl acyl radical comprising 2 to 6 carbon atoms, and a phenyl acyl radical; said phenyl being optionally substituted with one or more halogens, —$OCH_3$ or $C_1$–$C_6$ alkyl groups;

$R_{19}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, an alkyl acyl radical comprising 2 to 6 carbon atoms, and a phenyl acyl radical; said phenyl being optionally substituted with one or more halogens, —$OCH_3$ or $C_1$–$C_6$ alkyl groups;

$R_{20}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, and a benzyl group; said phenyl and benzyl groups being optionally substituted with one or more halogens, —$OCH_3$ or $C_1$–$C_6$ alkyl groups;

$R_{21}$ and $R_{22}$ are independently $C_1$–$C_6$ alkyl groups or form together a ring of 3 to 8 carbon atoms;

$R_{23}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, an alkyl acyl radical comprising 2 to 6 carbon atoms, and a phenyl acyl radical; said phenyl being optionally substituted with one or more halogens, —$OCH_3$ or $C_1$–$C_6$ alkyl groups;

$R_{24}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, an alkyl acyl radical comprising 2 to 6 carbon atoms, and a phenyl acyl radical; said phenyl being optionally substituted with one or more halogens, —$OCH_3$ or $C_1$–$C_6$ alkyl groups;

$R_{25}$ is selected from the group consisting of a $C_1$–$C_6$ alkyl group, a $C_2$–$C_6$ alkenyl group, a $C_2$–$C_6$ alkynyl group, a $C_3$–$C_8$ cycloalkyl group, a phenyl group, and a benzyl group; said phenyl and benzyl groups being optionally substituted with one or more halogens, —$OCH_3$ or $C_1$–$C_6$ alkyl groups;

B, C, D, and E are independently carbon or nitrogen;

F, G, H, and J are independently selected from the group consisting of carbon, nitrogen and sulfur, and with the proviso that only one of either F, G, H, or J can be sulfur, and with the further proviso that if one of either F, G, H, or J is sulfur, then $R_{15}$ is hydrogen or $x_4=0$.

2. A compound having the formula II:

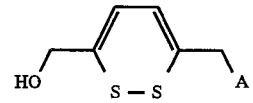

and pharmaceutically acceptable salts thereof, wherein:

A is selected from the group consisting of —OAr, —O(CO)Ar, —NH(CO)Ar, —S—Ar and B;

Ar is selected from the group consisting of phenyl, 1-imidazolyl, 2-imidazolyl, 3-imidazolyl, 4-imidazolyl, 5-imidazolyl, 2-pyridyl, 3-pyridyl, 4-pyridyl, 3-pyridazinyl, 4-pyridazinyl, 2-quinoxalinyl, 3-quinoxalinyl, 5-quinoxalinyl, 6-quinoxalinyl, 7-quinoxalinyl, 8-quinoxalinyl and 5-tetrazolyl; said Ar being optionally substituted with one or more groups selected from the group consisting of phenyl, —OH, —OR, —COOH, —N(R)(R), —F, —Cl, —Br, —I, —$CF_3$, —$CCl_3$, —$CBr_3$, —$CI_3$, —$NO_2$, a $C_1$–$C_{10}$ alkyl group, a $C_2$–$C_{10}$ alkenyl group, a $C_2$–$C_{10}$ alkynyl group, —C(O)O$C_1$–$C_{10}$ alkyl group, —C(O)O$C_2$–$C_{10}$ alkenyl group, —C(O)O$C_2$–$C_{10}$ alkynyl group and B;

each R is independently selected from the group consisting of H, a $C_1$–$C_{10}$ alkyl group, a $C_2$–$C_{10}$ alkenyl group and a $C_2$–$C_{10}$ alkynyl group; and B is a 5–7 membered saturated or unsaturated carbocyclic ring optionally having one or more heteroatoms selected from the group consisting of O, S and N; said B being optionally substituted with one or more groups selected from the group consisting of —OH, —OR, —COOH, —N(R)(R), —F, —Cl, —Br, —I, —$CF_3$, —$CCl_3$, —$CBr_3$, —$CI_3$, —$NO_2$, a $C_1$–$C_{10}$ alkyl group, a $C_2$–$C_{10}$ alkenyl group, a $C_2$–$C_{10}$ alkynyl group, —C(O)O$C_1$–$C_{10}$ alkyl group, —C(O)O$C_2$–$C_{10}$ alkenyl group, —C(O)O$C_2$–$C_{10}$ alkynyl group and =O.

3. A compound selected from the group consisting of:

3-(hydroxymethyl)-6-[(phenyloxy)methyl]-1,2-dithiin;

3-(hydroxymethyl)-6-[(pyridyl-2-oxy)methyl]-1,2-dithiin;

3-(hydroxymethyl)-6-[(pyrid-2-one-1-yl)methyl]-1,2-dithiin;

3-(hydroxymethyl)-6-[(pyridyl-3-oxy)methyl]-1,2-dithiin;

3-(hydroxymethyl)-6-[(3-hydroxyphenyloxy)methyl]-1,2-dithiin;

3-(hydroxymethyl)-6-[[3-(N,N-dimethylamino)-phenyloxy]methyl]-1,2-dithiin;

3-(hydroxymethyl)-6-[(3-hydroxypyridazin-6-one-1-yl) methyl]-1,2-dithiin;

3-(hydroxymethyl)-6-[(3-hydroxypyridazine-6-oxy) methyl]-1,2-dithiin;

3-(hydroxymethyl)-6-[(2-trifluoromethylphenyloxy) methyl]-1,2-dithiin;

3-(hydroxymethyl)-6-[(2-fluorophenyloxy)methyl]-1,2-dithiin;

3-(hydroxymethyl)-6-[(5-nitropyridyl-2-oxy)methyl]-1,2-dithiin;

3-(hydroxymethyl)-6-[(5-nitropyrid-2-one-1-yl)methyl]-1,2-dithiin;

3-(hydroxymethyl)-6-[(3-ethynylphenyloxy)methyl]-1,2-dithiin;

3-(hydroxymethyl)-6-[methyloxy[methylbenzoate-3-yl]]-1,2-dithiin;

3-(hydroxymethyl)-6-[methyloxy[3-hydroxyquinoxalin-2-yl]]-1,2-dithiin;

3-(hydroxymethyl)-6-[(2-chloro-5-trifluoromethylphenyloxy)methyl]-1,2-dithiin;

3-(hydroxymethyl)-6-[methyloxy[methyl benzoate-4-yl]]-1,2-dithiin;

3-(hydroxymethyl)-6-[(2-hydroxy-3-fluorophenyloxy-1-yl)methyl]-1,2-dithiin;

3-(hydroxymethyl)-6-[(1-hydroxy-3-fluorophenyloxy-2-yl)methyl]-1,2-dithiin;

3-(hydroxymethyl)-6-[methylthio-[1-(4-hydroxyphenyl)tetrazol-5-yl]-1,2-dithiin;

3-(hydroxymethyl)-6-[[4-(imidazol-1-yl)phenyloxy]methyl]-1,2-dithiin;

3-(hydroxymethyl)-6-[[(2,2-dimethyl-1,3-dioxolan-4-yl)methyloxy]methyl]-1,2-dithiin;

3,6-bis{[(2,2-dimethyl-1,3-dioxolan-4-yl)methyloxy]methyl}-1,2-dithiin;

3-(hydroxymethyl)-6-[methyloxy(2,3-dihydroxypropane-1-yl)]-1,2-dithiin;

3-[[(2,2-dimethyl-1,3-dioxolan-4-yl)methyloxy]methyl]-6-[[methyloxy(2,3-dihydroxypropane-1-yl)]]-1,2-dithiin;

3-(hydroxymethyl)-6-[methyloxy[methyl benzoate-2-yl]]-1,2-dithiin; and 3-(benzoyloxymethyl)-6-(hydroxymethyl)-1,2-dithiin.

4. A method for inhibiting the growth of a pathogen, comprising contacting said pathogen with a compound according to claim 1, wherein said pathogen is selected from the group consisting of *Candida albicans, Candida krusei, Candida parapsilosis, Candida tropicalis, Cryptococcus neoformans, Aspergillus fumigatus, Trichophyton rubrum, Epidermophyton species, Microsporum species, Sporothrix species, Blastomyces dermatitidis, Coccidiodes immiitis, Histoplasma capsulatum*, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdovirus, Togavirus, Hepadnavirus, *Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia,* Acinetobacter, *Enterobacter cloacae, Serratia marscens,* Listeria, Monocytogenes, *Enterococcus faecalis, Streptococcus pyogenes; Streptococcus pneumonia, Viridans streptococci, Haemophilus influenzae, Proteus mirabilis, Proteus vulgaris* and *Bacterioides fragilis.*

5. A method for inhibiting the growth of a pathogen, comprising contacting said pathogen with a compound according to claim 2, wherein said pathogen is selected from the group consisting of *Candida albicans, Candida krusei, Candida parapsilosis, Candida tropicalis, Cryptococcus neoformans, Aspergillus fumigatus, Trichophyton rubrum, Epidermophyton species, Microsporum species, Sporothrix species, Blastomyces dermatitidis, Coccidiodes immiitis, Histoplasma capsulatum*, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdovirus, Togavirus, Hepadnavirus, *Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia,* Acinetobacter, *Enterobacter cloacae, Serratia marscens,* Listeria, Monocytogenes, *Enterococcus faecalis, Streptococcus pyogenes; Streptococcus pneumonia, Viridans streptococci, Haemophilus influenzae, Proteus mirabills, Proteus vulgaris* and *Bacterioides fragilis.*

6. A method for inhibiting the growth of a pathogen, comprising contacting said pathogen with a compound according to claim 3, wherein said pathogen is selected from the group consisting of *Candida albicans, Candida krusei, Candida parapsilosis, Candida tropicalis, Cryptococcus neoformans, Aspergillus fumigatus, Trichophyton rubrum, Epidermophyton species, Microsporum species, Sporothrix species, Blastomyces dermatitidis, Coccidiodes immiitis, Histoplasma capsulatum*, Herpes virus, Influenza virus, Cytomegalovirus, human immunodeficiency virus, retrovirus, Adenovirus, Papillomavirus, Paravirus, Arenavirus, Bunyavirus, Coronavirus, Paramyxovirus, Picornavirus, Rhabdovirus, Togavirus, Hepadnavirus, *Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia,* Acinetobacter, *Enterobacter cloacae, Serratia marscens,* Listeria, Monocytogenes, *Enterococcus faecalis, Streptococcus pyogenes; Streptococcus pneumonia, Viridans streptococci, Haemophilus influenzae, Proteus mirabilis, Proteus vulgaris* and *Bacterioides fragilis.*

7. A pharmaceutical composition for use as an agent to inhibit the growth of a pathogen in warm-blooded animals, comprising a therapeutically effective amount of a compound of claim 1.

8. A pharmaceutical composition for use as an agent to inhibit the growth of a pathogen in warm-blooded animals, comprising a therapeutically effective amount of a compound of claim 2.

9. A pharmaceutical composition for use as an agent to inhibit the growth of a pathogen in warm-blooded animals, comprising a therapeutically effective amount of a compound of claim 3.

* * * * *